(12) United States Patent
Jennings-Spring

(10) Patent No.: US 7,905,852 B2
(45) Date of Patent: *Mar. 15, 2011

(54) SKIN-CONTACTING-ADHESIVE FREE DRESSING

(76) Inventor: Barbara Jennings-Spring, Jupiter, FL (US)

( * ) Notice: Subject to any disclaimer, the term of this patent is extended or adjusted under 35 U.S.C. 154(b) by 377 days.

This patent is subject to a terminal disclaimer.

(21) Appl. No.: 12/231,104

(22) Filed: Aug. 29, 2008

(65) Prior Publication Data

US 2009/0005722 A1 Jan. 1, 2009

Related U.S. Application Data

(63) Continuation-in-part of application No. 11/434,689, filed on May 16, 2006, now Pat. No. 7,645,252.

(51) Int. Cl.
*A61F 13/06* (2006.01)
*A61F 15/00* (2006.01)
*A61F 13/00* (2006.01)
*A61F 13/02* (2006.01)

(52) U.S. Cl. .......... 602/63; 604/304; 604/307; 604/308; 602/48; 602/58; 602/61; 602/901

(58) Field of Classification Search .......... 604/304, 604/307, 358, 385.01, 385.03, 385.04, 385.14, 604/387, 308, 174, 179–180; 602/41, 43, 602/53, 54, 61, 62, 79, 901

See application file for complete search history.

(56) References Cited

U.S. PATENT DOCUMENTS

| | | | |
|---|---|---|---|
| 1,615,945 A | 2/1927 | James | |
| 2,226,546 A | 12/1940 | Bower | |
| 2,387,642 A | 10/1945 | Calhoun | |
| 2,401,714 A | 6/1946 | Weil | |
| 2,564,183 A | 8/1951 | Wilson | |
| 2,646,796 A | 7/1953 | Scholl | |
| 2,882,528 A | 4/1959 | Tassie | |
| 3,263,681 A | 8/1966 | Nechtow et al. | |
| 3,710,790 A | 1/1973 | Lemon | |
| 3,834,380 A * | 9/1974 | Boyd | 604/180 |
| 3,880,159 A | 4/1975 | Diamond | |
| 4,165,748 A | 8/1979 | Johnson | |
| 4,176,664 A | 12/1979 | Kalish | |
| 4,333,468 A | 6/1982 | Geist | |
| 4,423,722 A | 1/1984 | Dickman | |
| 4,523,586 A | 6/1985 | Couri | |
| 4,569,348 A | 2/1986 | Hasslinger | |
| 4,576,599 A | 3/1986 | Lipner | |
| 4,617,017 A * | 10/1986 | Hubbard et al. | 604/179 |
| 4,855,294 A | 8/1989 | Patel | |
| 4,983,163 A | 1/1991 | Winans | |
| 5,074,315 A | 12/1991 | McCuiston | |

(Continued)

OTHER PUBLICATIONS

Office Action of Sep. 7, 2007 in parent U.S. Appl. No. 11/434,689 (9 pages).

(Continued)

*Primary Examiner* — Leslie R Deak
*Assistant Examiner* — Adam Marcetich
(74) *Attorney, Agent, or Firm* — McHale & Slavin, P.A.

(57) ABSTRACT

A dressing having a flexible sleeve shaped to accommodate a substantially cylindrical body portion, the sleeve having a lining which is substantially non-adherent to the body part being bandaged and having a peripheral securement means which attaches two peripheral portions to each other without those portions being circumferentially adhered to the sleeve portion.

22 Claims, 9 Drawing Sheets

U.S. PATENT DOCUMENTS

| | | |
|---|---|---|
| 5,085,210 A | 2/1992 | Smith, III |
| 5,158,556 A | 10/1992 | Starley |
| 5,163,914 A | 11/1992 | Abel |
| 5,163,943 A | 11/1992 | Mohiuddin et al. |
| 5,183,460 A | 2/1993 | Scherz |
| 5,209,718 A | 5/1993 | McDaniel |
| 5,269,788 A | 12/1993 | Nelson, III |
| 5,275,592 A | 1/1994 | Grizzaffi |
| 5,439,466 A | 8/1995 | Kilejian |
| 5,527,293 A | 6/1996 | Zamierowski |
| 5,592,953 A | 1/1997 | Delao |
| 5,618,302 A | 4/1997 | Martin |
| 5,642,525 A | 7/1997 | Ketola |
| 5,643,183 A | 7/1997 | Hill |
| 5,649,933 A | 7/1997 | Singh |
| 5,674,189 A | 10/1997 | McDowell et al. |
| 5,690,610 A | 11/1997 | Ito et al. |
| 5,722,575 A | 3/1998 | Smitth |
| 5,741,511 A | 4/1998 | Lee et al. |
| 5,769,808 A | 6/1998 | Matthijs et al. |
| 5,797,401 A | 8/1998 | Knight |
| 5,807,299 A | 9/1998 | McRoberts et al. |
| 5,817,038 A | 10/1998 | Orange et al. |
| 5,860,988 A | 1/1999 | Rawlings |
| 5,914,125 A | 6/1999 | Andrews et al. |
| 5,925,008 A | 7/1999 | Douglas |
| 5,935,091 A | 8/1999 | Friedman |
| 5,947,998 A | 9/1999 | Cartmoll et al. |
| 5,989,567 A | 11/1999 | Dolisi |
| 6,051,249 A | 4/2000 | Samuelson |
| 6,068,607 A | 5/2000 | Palmer |
| 6,290,653 B1 | 9/2001 | Che et al. |
| 6,307,118 B1 | 10/2001 | Reich |
| 6,309,344 B1 | 10/2001 | Werner |
| 6,311,933 B1 | 11/2001 | Starchevich |
| 6,378,745 B1 | 4/2002 | DeLuccia |
| 6,441,265 B1 | 8/2002 | Chan |
| 6,455,752 B1* | 9/2002 | Vesey ............................. 602/41 |
| 6,487,728 B1* | 12/2002 | Cook ............................... 2/403 |
| 6,580,011 B1 | 6/2003 | Jennings-Spring |
| 6,617,485 B2 | 9/2003 | Herzberg |
| 6,932,784 B1* | 8/2005 | Reading .......................... 602/61 |
| 7,645,252 B2* | 1/2010 | Jennings-Spring ............. 602/63 |
| 2001/0001883 A1 | 5/2001 | Wanzenreid |
| 2001/0047144 A1 | 11/2001 | Tillotson et al. |
| 2002/0095107 A1 | 7/2002 | Martin |
| 2002/0153013 A1 | 10/2002 | Single et al. |
| 2002/0195114 A1* | 12/2002 | Tollini |
| 2003/0050589 A1 | 3/2003 | McDevitt et al. |
| 2003/0093075 A1 | 5/2003 | Levinson |
| 2003/0131411 A1 | 7/2003 | Gibson |
| 2003/0139698 A1 | 7/2003 | Hyson |
| 2004/0019308 A1 | 1/2004 | Chow |
| 2004/0073152 A1 | 4/2004 | Karason et al. |
| 2006/0020236 A1 | 1/2006 | Ben-Nun |
| 2006/0200063 A1 | 9/2006 | Munro |
| 2007/0172432 A1 | 7/2007 | Stopek |
| 2008/0147045 A1 | 6/2008 | Alitalo |
| 2009/0317454 A1* | 12/2009 | Jennings-Spring ........... 424/449 |

OTHER PUBLICATIONS

Office Action of Feb. 26, 2008 in parent U.S. Appl. No. 11/434,689 (9 pages).

Advisory Office Action of Mar. 31, 2008 in parent U.S. Appl. No. 11/434,689 (3 pages).

Advisory Office Action of May 30, 2008 in parent U.S. Appl. No. 11/434,689 (3 pages).

Office Action of Nov. 24, 2008 in parent U.S. Appl. No. 11/434,689 (12 pages).

Office Action of Feb. 13, 2009 in parent U.S. Appl. No. 11/434,689 (12 pages).

International Search Report and Written Opinion of the International Search Authority in PCT/US2009/004808 filed Aug. 24, 2009.

Office Action of Nov. 24, 2008 in parent U.S. Appl. No. 11/434,689.

Phipps et al; Iontophoresis; Encyclopedia of Pharmaceutical Technology 2nd Edition, Swarbrick et al Eds. (Marcel Dekker, Inc., New York, 2002) pp. 1573-1587.

Sharma, et al; Transdermal drug delivery using electroporation. I. Factors influencing in vitro delivery of terazosin hydrochloride in hairless rats; Journal of Pharmaceutical Sciences 89: 528-535 (2000).

Tang, et al; Effects of low-frequency ultrasound ont he transdermal permeation of mannitol: Comparative studies with in vivo and in vitro skin; Journal Pharmaceutical Sciences 91: 1776-1794, 2002.

Doukas, et al; Transdermal drug delivery with photochemical waves; Lasers and Electro-Optics Society vol. 1, No. 1, 1999; pp. 360-361 (Summary).

Bioelectronics: Home, http://www.bioelectronicscorp.com 4pages.

World's first transdermal insulin shows promise; http://www.in-pharmatechnologist.com Jun. 19, 2006.

Clotting Agents; LawOfficer.com; Law Office Magazine vol. 4, Issue 3; http://www.lawofficer.com/news-and-articles/articles/lom/0403/Clotting_Agents.html (6 pages).

Hemcon product information; How Hem Con Dressings Work; http://www.hemcon.com/EducationCenter/HowHemConDressigsWork.aspx.

\* cited by examiner

SKIN-CONTACTING-ADHESIVE FREE DRESSING

CROSS-REFERENCE TO RELATED APPLICATIONS

This application is a continuation-in-part of U.S. Ser. No. 11/434,689, filed May 16, 2006 now U.S. Pat. No. 7,645,252, which is incorporated herein by reference in its entirety.

STATEMENT REGARDING FEDERALLY SPONSORED RESEARCH OR DEVELOPMENT

Not Applicable

FIELD OF THE INVENTION

The invention relates to transdermal drug delivery for injured body parts and organs in need of pharmaceutical interventions without the need for an adhesive in contact with the skin. The administration areas where the compounds can be delivered are body parts that are primarily cylindrical in shape. For example, the arm, leg, torso, finger, toes, will be most advantageous to place the adhesiveless unit/dressing for therapeutic interventions.

The invention further relates to various transdermal and topical drug applications in a variety of contexts without the need for skin-contacting adhesives. These include such bandages with or without energy sources for supplementally driving the drug into or through the skin and includes, without limitation such systems as iontophoretic, sonophoretic, pulsed electronic, photophoretic, etc. In these topical and/or transdermal application, the body part being treated need not be injured or wounded, but the application of the therapeutic agent or other material can be for the expression of an effect at other parts of the person, animal being treated. Drug formulations from which active agents are delivered vary over a wide range and include, without limitation, solutions, dispersions, emulsions, liposomal encapsulations, dispersions in solids such as monolithic polymers, etc. They include formulations in currently marketed transdermal products, inotophoretic products, sonophoretic products, and photophoretic products to name a few. Where the active agent can be made into a readily soluble form (such as formulations of the "orally disintegrating type"), they can also be used as dry materials embedded or absorbed in one or more layers which will be wetted, either directly from the skin contact site or by briefly wetting or hydrating either the skin contact site or the dressing at about the time of application. Dispersions of active agents in adhesives are also suitable formulations for the represent invention provided that the adhesive used does not come in contact with the skin or wound being dressed.

BACKGROUND OF THE INVENTION

Bandage application for applying medications to compromised skin, whether merely slightly broken (scrapes or small cuts) or severely compromised such as in severe large scale burns require bandages to be very gingerly applied and removed so as to avoid disturbing the healing process. Transdermal and topical bandages usually have adhesives associated therewith that adhere to skin very well and make it difficult to remove and change bandages without significant pulling on skin or causing substantial stresses and torques on the injured area. These situations result in re-injury to the healing site or further opening and sometimes expanding would area, even when the adhesive is on the periphery of the wound site. Further, where the skin or wound area being dressed has scabs, friability, or hairs, the removal of adhesives from the skin can be painful. In addition, in older patients, or those with arthritic conditions, the removal of adhesive dressings can be quite difficult.

In many transdermal contexts, whether with or without the foregoing issue, a significant difficulty involves skin irritation, frequently due to the skin-contacting adhesives being utilized to secure the transdermal to the body. Because of such irritation, transdermal patches have traditionally been made as small as possible so that as small a region as possible is affected (and leaving alternate application sites for rotation of application of subsequent dosages while the prior application site recovers). The size limitation of the transdermal patch means that for many drugs, the formulations must have a flux enhancer in order to achieve a sufficient delivery rate (inherent delivery rate/unit area X area of application) for an efficacious product. Unfortunately, flux enhancers frequently are themselves irritating to the skin and thus, more times than not, just exacerbate the problem. Still other drugs, even with the flux enhancers, have insufficient delivery rates from trandermals of the conventional sizes.

In further contexts, certain drugs have been incompatible with various adhesives (chemical or physical instability of the drug) or plasticize (or "soften") the adhesive through which it must pass or in which it is embedded), meaning that the number and kind of adhesives that can be used are limited, often leaving only the more irritating adhesives as the only suitable ones, or resulting in devices in which the drug containing layer partially pulls away from the device when its "release liner" is removed or the device tends to fall off the patient prematurely, either way resulting in underdosing of the patient.

Some attempts have been made to increase drug flux through the skin, with and without permeation enhancers by using various energy sources to help drive the material through the skin. These include iontophoretic systems (utilizing charged moieties and applied current), sonophoretic systems (utilizing ultrasonication), photophoretic systems (utilizing (generally non-ablative) laser energy), etc. Other attempts have been made using liposomal encapsulation to take advantage of liposomal transport and fairly recently nanoenapsulation (delivery of proteins such as insulin and other large molecules across skin).

The present invention addresses these issues in the transdermal context by removing the need for the skin-contacting adhesive, allowing the size of the transdermal to be increased, which then permits efficacious delivery of materials with lower inherent flux rates as the total delivery per unit time is increased ((inherent flux)×(area of device)). This allows for reduction or elimination of the flux enhancers, so as to further avoid skin irritation, and allows for the application of transdermal technology to a range of molecules to which it could not be applied previously. The coupling of the present dressing devices with or the incorporation within the present dressing devices of various driving energy structures (iontophoretic, sonophoretic, pulsed electronic, and/or photophoretic) further expands the range of molecules that can be delivered, as does the use of liposomal and nanoencapsulations.

OBJECTS OF THE INVENTION

It is therefore an object of the invention to provide a dressing for a substantially cylindrically shaped body part with a securement means allowing the dressing to be applied and removed with the proper amount of pressure in order to promote hemostasis.

It is yet another object of the invention to provide a dressing for an animal or human substantially cylindrical body part that permits easy removal of the dressing without involving the bandaged part in the removal process.

Yet another object of the invention is to provide a surgical dressing which preserves hygienic conditions by providing an improved securement means.

A still further object of the invention is to provide a bandage suitable for at least one of (a) maintaining hemostasis; (b) topical administration of an agent, or (c) transdermal administration of an agent without the need for a skin-contacting-adhesive.

Another object of the invention is to provide a skin-contacting adhesiveless transdermal device for active agents that are poorly skin penetrating without the use of or with lesser amounts of skin penetration enhancers.

Another object of the invention is to provide a dressing containing an active agent which maintains a higher total flux due to larger skin contacting surface area than the traditional transdermals having the same agent.

An even further object of the invention is to provide a skin-contacting-adhesiveless transdermal device in conjunction with an energy source and energy delivering means to provide an iontophoretic, sonophoretic, or photophoretic driving energy to aid in the delivery of a therapeutic entity.

Even further objects of the invention will be apparent to those of ordinary skill in the art.

BRIEF SUMMARY OF THE INVENTION

These and other objects of the invention are surprisingly achieved by a dressing having a flexible sleeve shaped to accommodate a substantially cylindrical body or plant portion, the sleeve having a lining which is substantially non-adherent to the body or plant part being bandaged or dressed and having a peripheral securement means which attaches two peripheral portions to each other without those portions being circumferentially adhered to the sleeve portion. The dressing can be used to dress a wound without medication, can be used to apply medications to a wound, either topically or transdermally, with or without the aid of supplemental driving energy sources, to a wounded or painful area, can be used to apply medications transdermally to one body part (with or without auxiliary driving energy) to one body part area for local action or for systemic action at one or more sites distant from the application site.

BRIEF DESCRIPTION OF THE DRAWINGS

Embodiments that are presently preferred are shown in the drawings; however, the invention is not limited to the precise arrangements and instrumentalities shown, wherein:

FIG. 15A is an enlarged view of the sleeve portion of a present invention device into which the body part is to be inserted, while

DETAILED DESCRIPTION OF THE INVENTION

The present invention (shown with respect to particular embodiments in FIGS. 1-20) is generally directed to a dressing having a flexible sleeve portion or tubular shaped portion shaped to accommodate a substantially cylindrical body or plant portion, the sleeve portion or tubular shaped portion having a lining which is substantially non-adherent to the body or plant part being bandaged or dressed and having a peripheral securement means which attaches two peripheral portions to each other without those portions being circumferentially adhered to the sleeve portion. FIGS. 1-5 show the various views of a device (1) of the invention in a closed position about a body part that has been inserted through sleeve opening 11, although only FIG. 1 (of FIGS. 1-5) shows the body part (dotted line). The remaining elements of these FIGS. 1-5 are described more specifically with respect to FIGS. 6-10 below.

Figure 1:
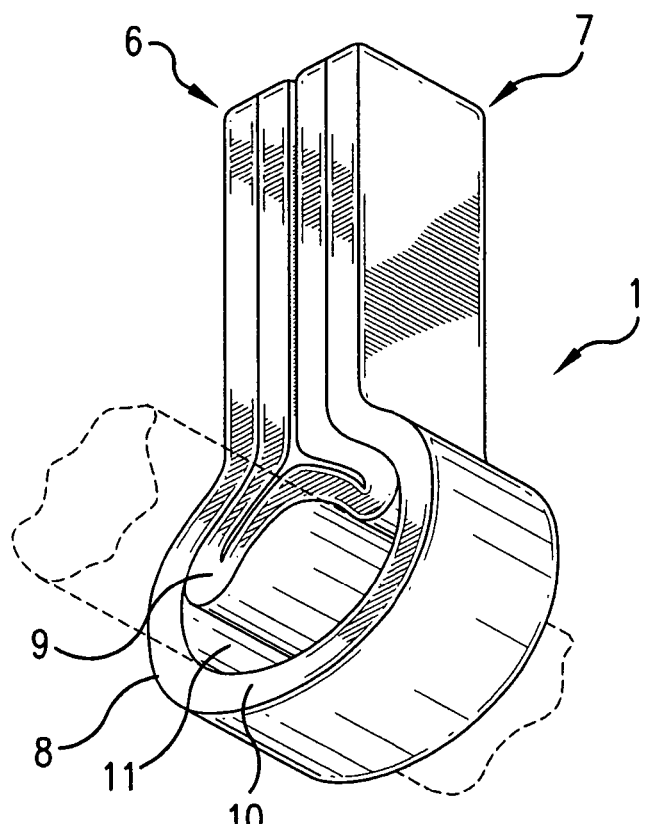
FIG. 1 is a perspective view of a device of the present invention secured around a body or plant part.
Figure 2:
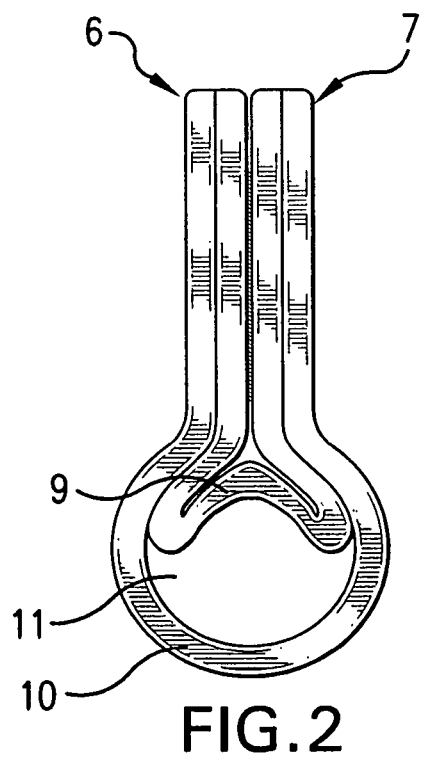
FIG. 2 is a front view of the device of FIG. 1 in the secured position (omitting the body part around which it is secured.
Figure 3:
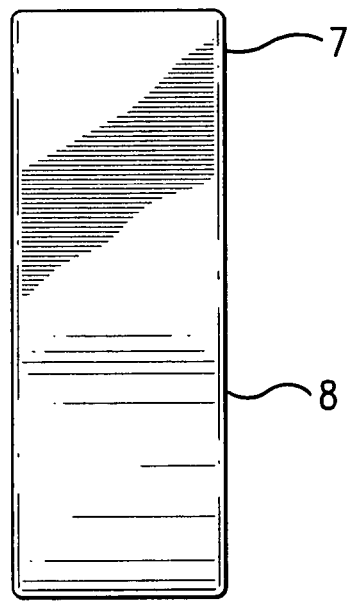
FIG. 3 is side view of the device of FIG. 1 in the secured position.
Figure 4:
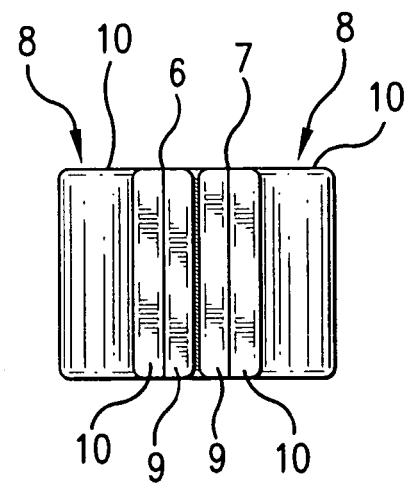
FIG. 4 is a top view of the device of FIG. 1 in the secured position.
Figure 5:
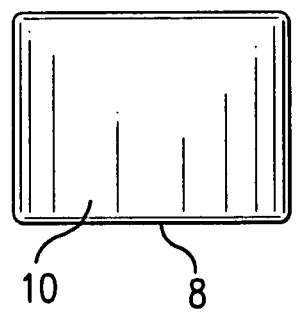
FIG. 5 is a bottom view of the device of FIG. 1 in the secured position.
Figure 6:
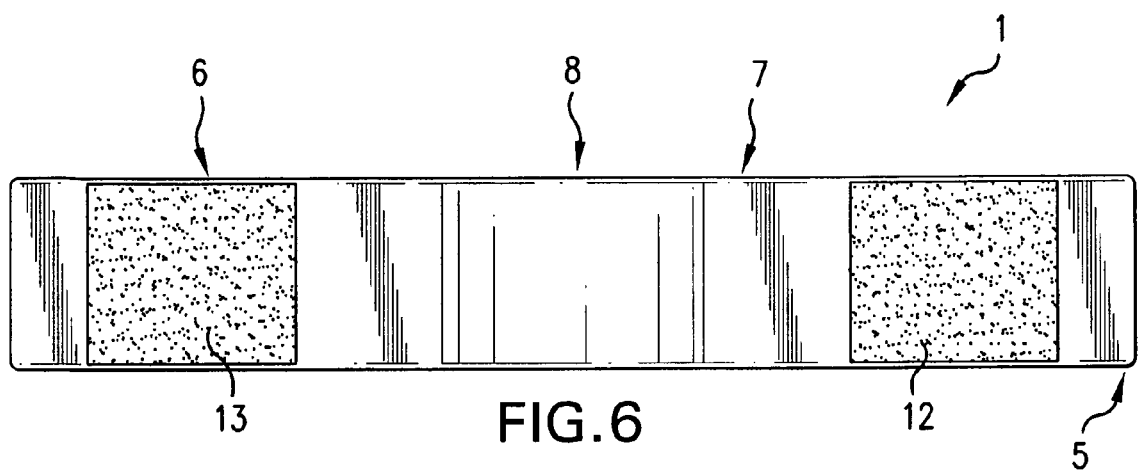
FIG. 6 is a top planar view of the device of FIG. 1 in pre-use unfolded position.
Figure 7:
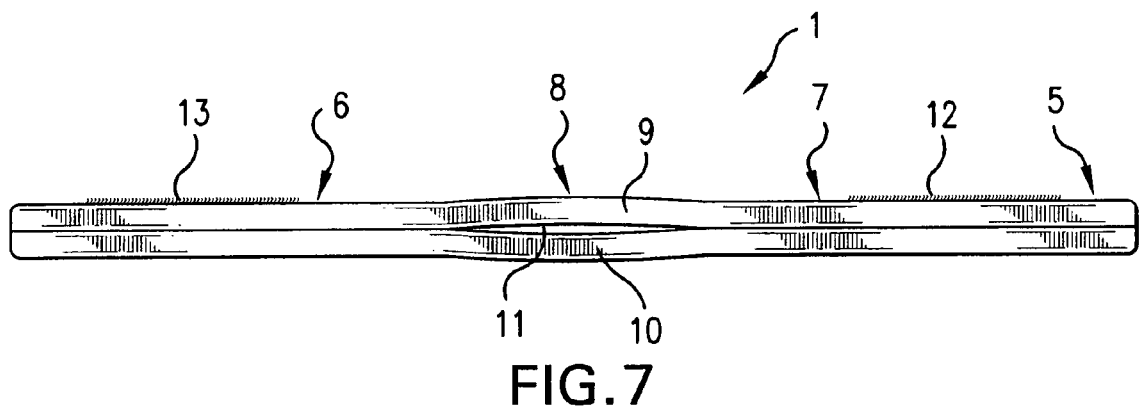
FIG. 7 is a front planar view of the device of FIG. 1 in pre-use unfolded position.
Figure 8:
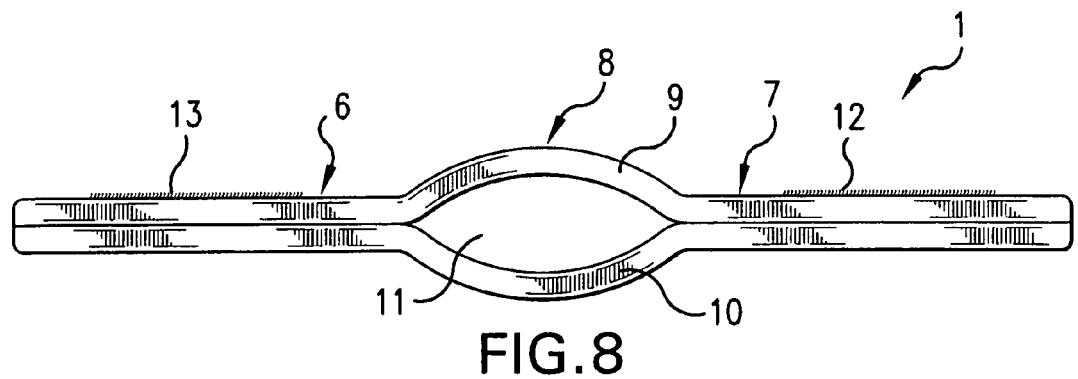
FIG. 8 is a front planar view of the device of FIG. 7 in pre-use unfolded position that has been opened for use.
Figure 9:
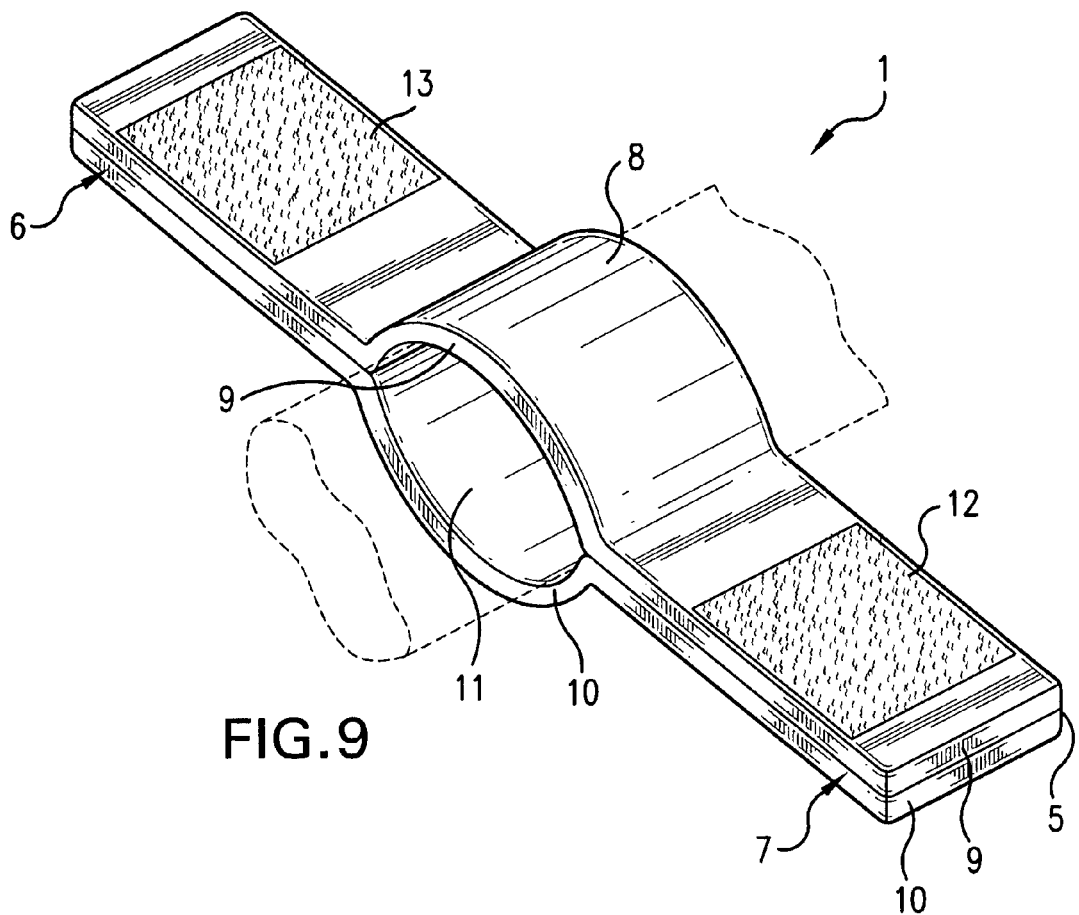
FIG. 9 is perspective view of the device of FIG. 8 showing placement on the body part being dressed prior to closure for securement.
Figure 10:
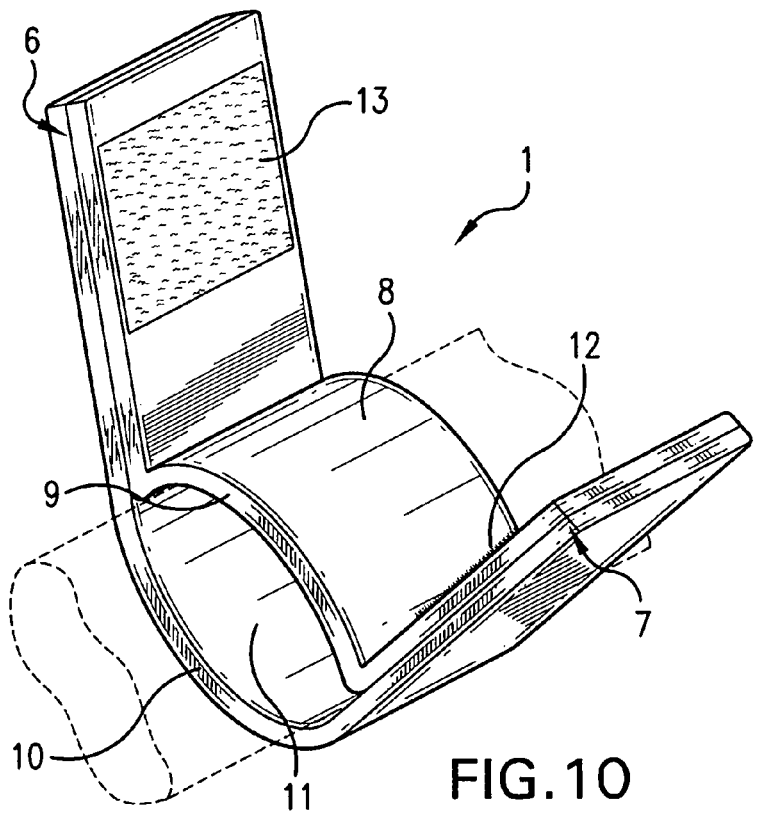
FIG. 10 is a perspective view of the device in FIG. 9 showing partial displacement of the peripheral flaps in the act of securing the device.

In FIGS. 6 and 7, the invention device 1 is shown in a flat, pre-use, unopened position and is shown as generally elongated member 5. Generally elongated member 5 is divided into left and right flaps 6 and 7 and a central portion 8. Generally elongated member 5 is bifurcated into a top portion 9 and a bottom portion 10, which are adhered to each other in the left and right flap portions 6 and 7, but not in central portion 8 so as to create between them sleeve opening 11 in central region 8. When flap portions 6 and 7 are displaced centrally inward, top portion 9 and bottom portion 10 can be displaced from one another such as shown in FIG. 8 to open sleeve 111 in anticipation of applying the device to an appropriate body or plant part. Securement means 12 and 13 are placed so that once the device is placed on the body or plant part, the peripheral ends of flaps 6 and 7 (distal from central portion 8) can be grasped and brought together so that securement means 12 and 13 are substantially mated to one another (face to face) and result in securing the device in place without adhering to central portion 8. In the course of bringing flaps 6 and 7 together, the top portion 9 may fold into a position as shown more specifically in FIGS. 1 and 2. It should be noted that although the figures show the securement means across a substantial portion of the flaps 6 and 7, the area of flaps 6 and 7 having a securement means thereon can vary in both length and width as desired so long as the securement means, when moved to a closed position about a body part do not adhere to circumferential areas of the central portion 8, but only to securement means areas. An alternative embodiment has flaps 6 and 7 extending a minimum distance from central portion 8 and has securement means extensions therefrom so that when brought together into a closed position about a body part, flap portions 6 and 7 may or may not meet each other, but the securement means extension thereof do meet each other in a way that allows for the securement means to mate to each other and secure the device in place without attaching to the central portion 8.

Figure 11:
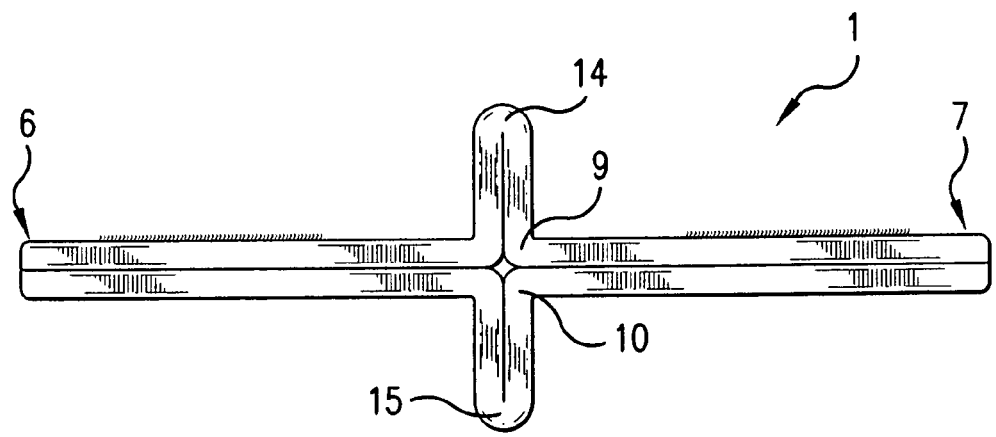
FIG. 11 is a front planar view of a device of 7 in a first alternate pre-use folded position.
Figure 12:
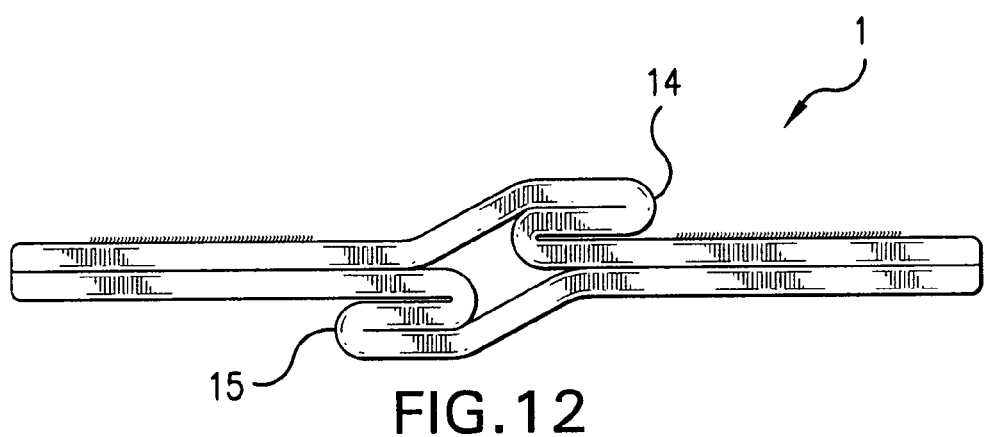
FIG. 12 is a front planar view of a device of 7 in a second alternate pre-use folded position.
Figure 13:
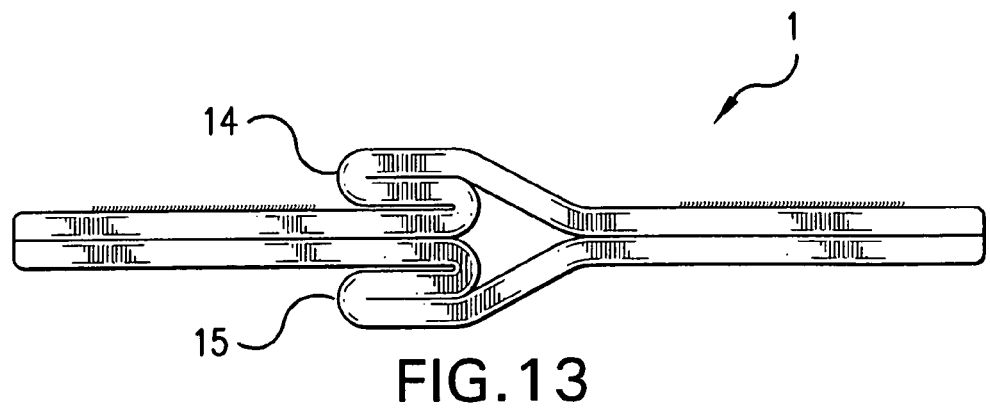
FIG. 13 is a front planar view of a device of 7 in a third alternate pre-use folded position.

FIGS. 11-13 show the device of FIG. 7 in which the device is in alternate pre-use folded positions rather than the flat opened position of FIGS. 6 and 7. In FIGS. 11-13, the peripheral ends of the flaps 6 and 7 (distal from the central portion 8) have been displaced centrally, but instead of opening the sleeve portion as in FIG. 8, the central portion 8 has not been opened, resulting in an upper minor flap 14 and a lower minor flap 15. FIGS. 12 and 13 show the device of FIG. 11 where the minor flaps have been displaced to opposite sides (FIG. 12) or to the same side (FIG. 13). For FIGS. 12 and 13, left and right may be interchanged without departing from the present invention. When positions such as those in FIGS. 12 and 13 are utilized, one must be sure that the securement means chosen is one which would not result in attachment between either of the flaps 6 and 7 on the one hand and flaps 14 and 15 on the other. Other alternate pre-use folded positions will be apparent to those of ordinary skill in the art without departing from the present invention. As an alternative, a securement means cover (not shown) which is not adherent to the other portions of the device in which it comes in contact may be used to prevent adherence of the securement means to other layers during manufacture, packaging, and storing of the device until such time as one is ready to apply the device. Suitable materials include any material which is easily removed when desired from the securement means and yet prevents adherence between the securement means and the rest of the device when in place. For example, when the securement means is Velcro, the securement means cover may be a piece of mated Velcro or a non-Velcro sleeve slipped over the securement means. Alternatively, where the securement means is an adhesive, the securement means is a releasable liner that can be easily removed from such adhesive. Where the securement means is a snap, no securement means cover is needed. It should be noted that securement means covers are not required and merely optional, but may, in fact, be preferred.

Figure 14A:
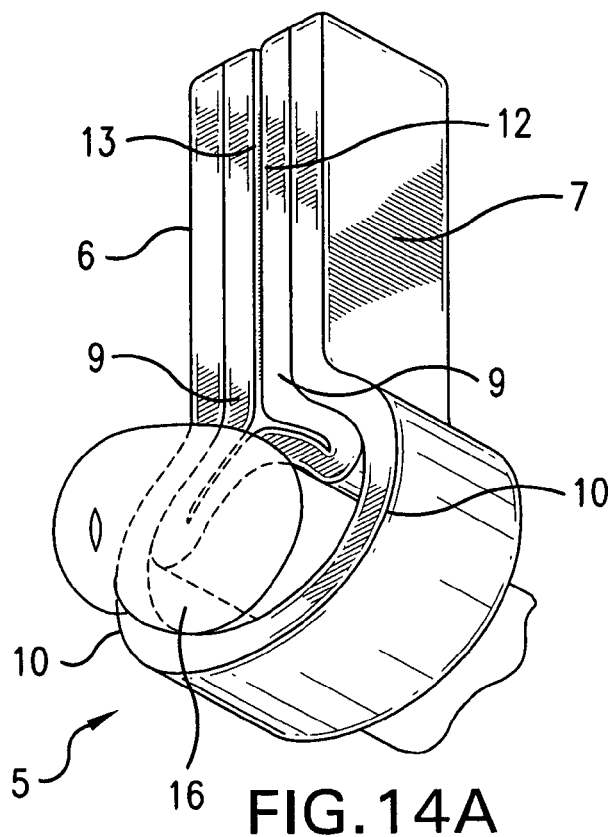
FIGS. 14 A and B are perspective views of an invention device applied in the context of a penile dressing.
Figure 14B:
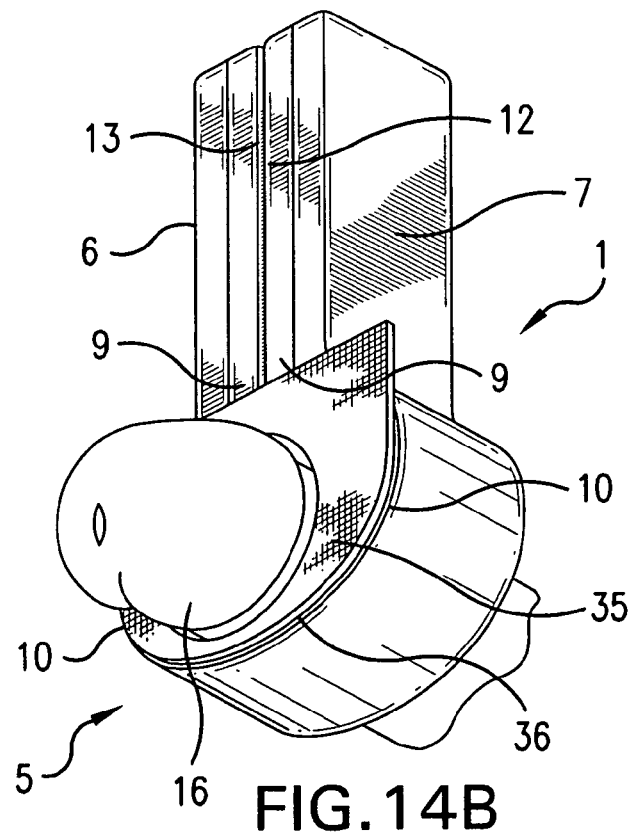

FIGS. 14 A and B show an embodiment of the present invention as applied and secured to a wounded penis 16 (such as after circumcision). As shown, the device has been applied to the penis, and right and left flaps 6 and 7 pulled together so as to allow securing means 12 and 13 to mate and secure the device. FIG. 14 B shows the same arrangement as FIG. 14A except that a drainage member 35 (preferably a mesh fabric material) is also present, which is affixed to portion 10 in any suitable manner, such as by stitching 36. The orientation and shape of drainage member 35 is not critical and many other variations will be appreciated by those of ordinary skill. While drainage member 35 helps to isolate the circumcised penis, it is merely optional in the present invention.

Figure 15A:
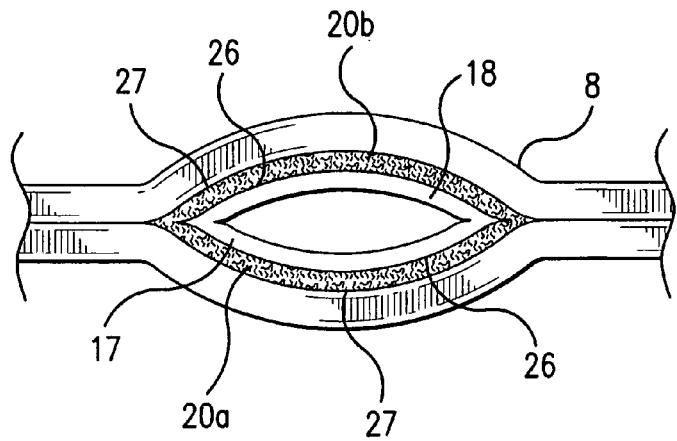
Figure 15B:
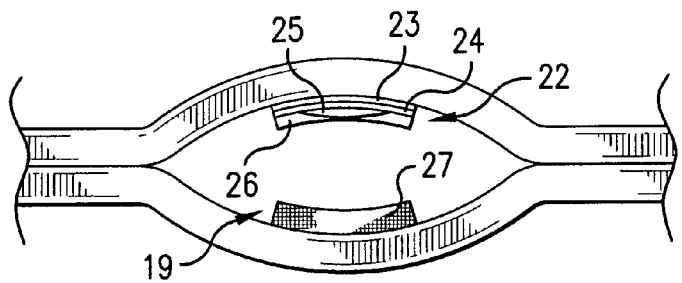
FIG. 15B shows a device of the invention wherein the active agent is contained within transdermal portions adhered to at least a portion of the skin contacting surface.
Figure 16:
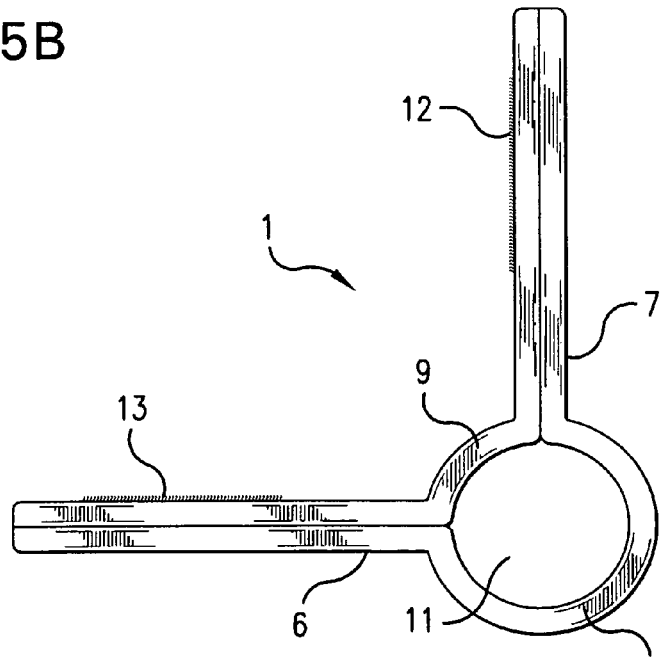
FIG. 16 shows an alternate embodiment of the present invention in an open position ready for use.
Figure 17:
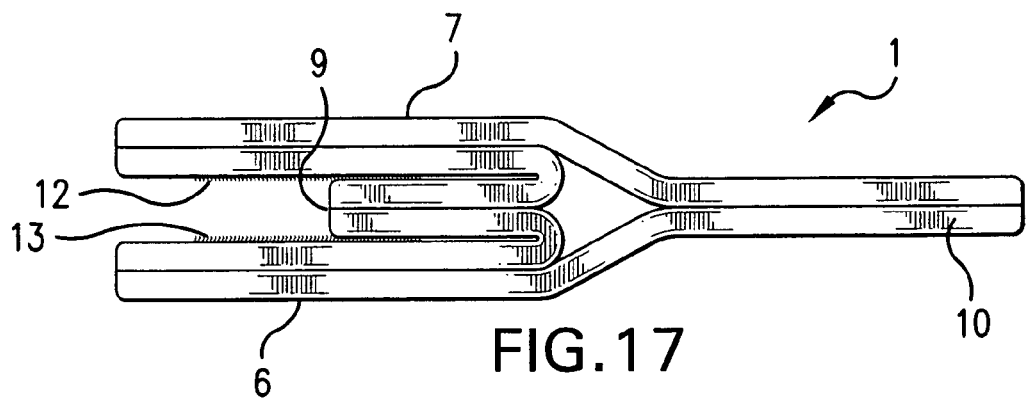
FIG. 17 shows the embodiment of FIG. 16 in a pre-use first folded position.
Figure 18:
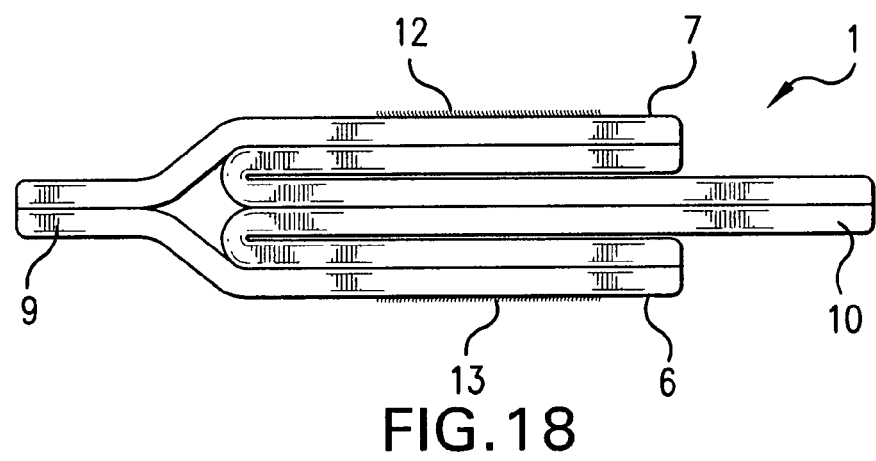
FIG. 18 shows the embodiment of FIG. 16 is a pre-use second folded position.
Figure 19:
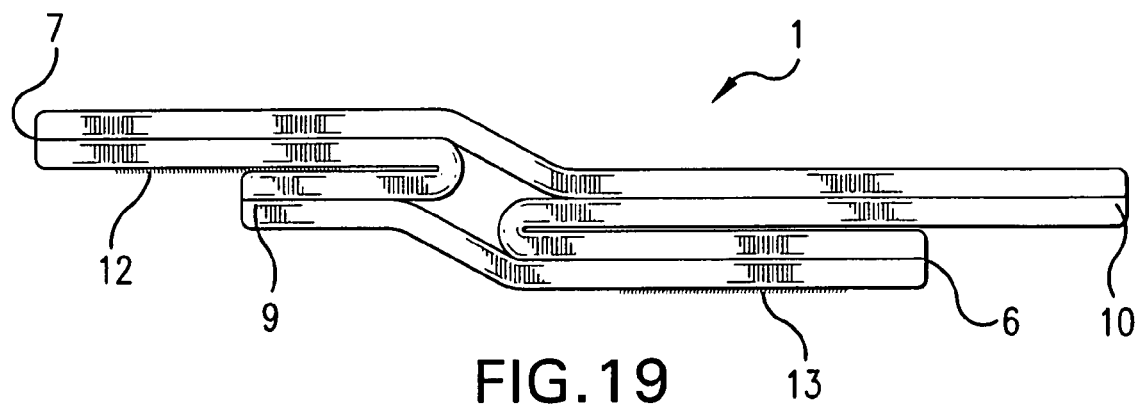
FIG. 19 shows the embodiment of FIG. 16 in a pre-use third folded position.

FIG. 15A is an enlarged view of central portion 8 of FIG. 8, showing the details of the protecting surfaces of the bandage portion which will impact against the body part or plant part to which the invention dressing is being applied. Generally, the center portion 8 includes an outer wall 27 formed by the outside surfaces of portions 20A and 20B and an inner wall 26 formed by the inner portions of opposing portions of 20A and 20B. Portions 20A and 20B may be gauze or any other suitable material. Lining portions 17 and 18 can be fitted flushly against the inner wall 26 and sandwiched between opposing portions 20A and 20B. While FIG. 15 shows portions 20A and 20B as only in the central portion 8, alternative and preferred embodiments have portions 20A and 20B extending partially into or completely across the left and right flap regions 6 and 7. In many embodiments, lining portions 17 and 18 are merely a coating which prevents adhesion or sticking of the device to the skin, such as petrolatum, which can be applied in the manufacturing process or can be added by the user at the time of use. Additionally, portion 20A and lining portion 17 may constitute a unitary layer if the material of portion 20A is naturally skin-non-adherent or is impregnated with a materials so as to be skin non-adherent. Xeroform® (petrolatum impregnated gauze with 3% bismuth tribromophenate) is one such suitable material (although the bismuth tribromophenate should preferably not be used with infants). Similarly, portion 20B and lining portion 18 may also constitute a unitary layer in the same fashion. The inner surface of central portion 8 (i.e., the lining portions 17 and 18 if present, or the portions 20A and 20B if lining portions 17 and 18 are not separately present), may additionally be impregnated with suitable active agents or formulations thereof for any of a variety of uses. Lining portions 17 and 18 or portions thereof, alone or together with corresponding segments of portions 20A and 20B may be transdermal formulations or transdermal devices that have been adhered to wall 27 (if lining portions 17 and 18 and portion 20A and 20B are otherwise not separately present in the respective area) or adhered to wall 26 (if lining portions 17 and 18 are not present but portions 20A and 20B are present in the corresponding area). One variant of this is shown in FIG. 15B, where two different transdermal regions are present using two different types of transdermal delivery. Use of transdermal delivery with the present invention can utilize a single transdermal delivery over all or a portion of the skin-contacting surface or as shown in FIG. 15 utilize different transdermal delivery portions that are the same or different from one another in the same device. In FIG. 15B, one portion of surface 27 carries a monolithic drug delivery portion 19 having one or more active agents dispersed in a non-skin-contacting adhesive polymeric material, which may be cast directly on surface 27 (or onto surface 26 if portion 20A is present) or precast and fastened onto surface 27 (or onto surface 26) using a suitable adhesive. A second drug delivery portion 22 of the "reservoir pouch type" which generally comprises a drug-non-permeable (usually occlusive) backing 24, a drug permeable overlayer 26, backing 24 and overlayer 26 defining reservoir area 25 therebetween in which a liquid or semisolid drug formulation is contained, and an adhesive for adhering the backing layer to surface 27 (or to surface 26 if it is present). Generally, drug delivery portion 22 will be premanufactured and adhered to the appropriate layer of the invention device in the course of manufacture. However, where desired, premanufacture is not required and the drug delivery portions 19 and 22 can be integrated in the overall device manufacture process. In either case, where permeable drug delivery devices 19 and/or 22 are utilized additional barrier layers to prevent migration of the drug before use may be desirable (such as removable drug-non-permeable release liners, and barrier backings where the surface 27 or 26 is drug permeable) and those of ordinary skill will be well aware appropriate materials and placement thereof. Alternatively, premanufactured drug delivery devices 19 and 22 may be adhered with appropriate adhesives to surface 27 or 26 of the devices of the present invention at the time that the device is about to be applied to a particular body part. This allows for extensive variation in the type of drug to be applied as the particular case may call for. Drug delivery devices 19 and 22 may be designed for either merely topical delivery of drug or transdermal delivery, either locally or systemically as the case may be, without departing from the present invention. In the situation where the therapeutic agent is dispersed in an adhesive monolithic layer, some material which is not adhesive to skin needs to be interposed between the skin and the surface of the monolithic adhesive layer that would otherwise be in contact with the skin. This can be by overcoating the adhesive monolith on the potential skin-contacting surface with a therapeutic agent permeable non-adhesive material or by interposing a fabric layer between the monolith and the skin. Where desired, the dressing can be generically constructed with an "insert pouch" being framed by one or more woven or nonwoven, suitably skin-non-adherent gauze) layers and a prefabricated transdermal can be inserted and the adhesive layer of the transdermal adheres to the pouch interior. Where desired, the skin-contacting side of the "pouch" can be made from rapidly hydrolysable polymeric materials such as for example, without limitation, poly(lactic-co-glycolic acid) (PLGA). These polymers are well known in the art and have been used in grafts, sutures, implants, and prosthetic devices. Other useful biodegradable polymers include polycaprolactone, polyglycolide, polylactic acid, and poly 3-hydroxybutyrate, to name a few. Other variations will be apparent to those of ordinary skill.

With respect to the active agents, reference to a free acid or base is intended to include reference to salts, esters, and amides thereof and vice versa, while reference to a compound that contains asymmetric centers is intended to include each of the individual optical isomers thereof and mixtures of optical isomers and reference to an individual optical isomer is intended to include reference to other optical isomers of the compound mentioned and mixtures therewith.

Most frequently, such active agents will include (but none is absolutely required), without limitation,
(a) Anti-infectives such as, without limitation,
(i) topical anti-infectives (such as, without limitation, aminocrine, benzethonium chloride, bithionolate salts, bromchlorenone, cetalkonium halide, chlorhexidine, clioquinol, domiphen halide, fentichlor, fludazonium, furazolidone, gentian violet, halquinols, hexachlorophene, imedecyl iodine, iodine, mafenide acetate, meralein, methylbenzethonium chloride, nitrofurazone, nitrmersol, octenidine, oxychlorosene, povidone-iodine, silver nitrate, sulfadiazine, symclosene, thimerfonate, thimerosal, and troclosene);
(ii) antibacterials and antibacterial matrices (such as without limitation, alamecin, alatrofloxacin, alexidine, amidinocillin, amicycline, amifloxacin, amikacin, amoxicillin, amphomycin, ampicillin, apalcillin, apramycin, aspartocin, asperlin, astromycin, avilamycin, avoparcin, azithromycin, azlocillin, bacampicillin, bacitracin, bambermycins, berythromycins, betamicin, biapenem, biniramycin, biphenamine, butikacin, butirosin, carbadox, carbenicillin, carumonam, cefaclor, cefadroxil, cefamandole, cefaparole, cefatirazine, cefazaflur, cefbuperazone, cefdinir, cefepime, cefetecol, cefixime, cefinenoxime, cefinetazole, cefonicid, cefoperazone, ceforanide, cefotaxime, cefotetan, cefotiam, cefoxitin, cefpimizole, cefpiramide, cefpirome, cefpodoxime, cefprozil, cefroxadine, cefulodin, ceftazidime, ceftibuten, cceftizoxime, ceftriaxone, cefuroxime, cefacetrile, cephalexin, cephaloglycin, cephaloridine, cephalothin, cephapirin, cephadrine, cetocycline, cetophenicol, chloramphenicol, chlortetracycline, cinoxacin, ciprofloxacin, clarithromycin, clinafloxacin, clindamycin, cloxacillin, cloxyquin, colistimethate, coloistin, coumermycin, cyclacillin, dalfopristin, daptomycin, demeclocycline, demecycline, diaveridine, dicloxacillin, dihydrostreptomycin, dirithromycin, doxycycline, droxacin, enoxacin, eperezolid, epicillin, epitetracycline, erythromycin, fleroxacin, floxacillin, fludalanine, flumequine, fosfomycin, fumoxicillin, furozolium, fusidate, fusidic acid, gatifloxacin, gentmicin, gloximonam, gramicidin, grepafloxacin, haloprogin, hetacillin, hexedine, ibafloxacin, imipenem, josamycin, kanamycin, kitasamycin, levofloxacin, levopropylcillin, lexithromycin, lincomycin, linezolid, lomefloxacin, loracarbef, mafenide, meclocycline, megalomicin, mequidox, meprpenem, methacycline, methicillin, metioprim, mezlocillin, minocycline, mirinamycin, nafcillin, nalidixic acid, nebramycin, neomycin, netilmicin, neutramycin, nifuradene, nifuraldezone, nifuratrone, nifurdazil, nifurimide, nifurpirinol, nifurquinazole, nifurthiazole, nitrocycline, norfloxacin, novobiocin, ofloxacin, ormetoprim, oxacillin, oximonam, oxolinic acid, oxytetracycline, paldimycin, paulomycin, pefloxacin, penamecillin, penicillin G, penicillin V, pentizidone, piperacillin, pirbenicillin, pirlimycin, pivampicillin, polymixin, propikacin, quindecamine, quinupristine, racephenicol, ramoplanin, ranimycin, relomycin, repromicin, rifametane, rifamexil, rifamide, rifampin, rifapentine, rifaximin, rolitetracycline, rosaramicin, rosoxacin, roxarsone, roxithromycin, sancycline, sanfetrinem, sarmoxicillin, sarpicillin, sisomicin, sparfloxacin, spectinomycin, spiramycin, stallimycin, streptinocozid, sulfabenzamide, sulfacetamide, sulfacytine, sulfadiazine, sulfadoxime, sulfalene, sulfamerazine, sulfameter, sulfamethiazine, sulfamethiazole, sulfamethoxazole, sulfamonothoxine, sulfamoxole, sulfanilate, sulfasalszine, sulfasomizole, sulfathiazole, sulfazamet, sulfisoxazole, sulfomyxin, sulopenem, sultamicillin, suncillin, talampicillin, teicoplanin, temocillin, tetracycline, tetroxoprim, thiamphenicol, thiphencillin, ticarcillin, tiodonium, tobramycin, tosufloxacin, trimethoprim, trisulfapyrimidines, troleandomycin, trospectmycin, trovafloxacin, tyrothricin, vancomycin, zorbamycin or mixtures thereof; preferably bacitracin, neomycin, polymixin or mixtures thereof);
(iii) antifungals such as, without limitation, acrisorcin, ambruticin, amphotericin B, azaconazole, azaserine, basifungin, bifonazole, butenafine, butoconazole, candicidin, carbol-fuchsin, chlordantoin, ciclopirox, cilofungin, cisconazole, clotrimazole, denofungin, dipyrithione, doconazole, econozole, enilconazole, ethonam, fenticonazole, filipin, fluconazole, flucytosine, fungimycin, griseofulvin, hamycin, isoconazole, itraconazole, kalafungin, ketoconazole, lomofungin, lydimycin, mepartricin, metacresol, miconazoile, naftifine, nifuratel, nifuramerone, nitralamine, nystatin, octanoic acid, omoconazole, orconazole, oxiconazole, oxifungin, parconazole, pyrrolnitrin, rutamycin, sanguinarium, saperconazole, scopafungin, sinefungin, sulconazole, terbinafine, terconazole, thiram, ticlatone, tioconazole, tolciclate, tolindate, tolnaftate, triacetin, triafungin, undecenylate, zinoconazole, and mixtures thereof);

(iv) and mixtures thereof, broad spectrum anti-infectives being preferable over others;

(b) Local anesthetics (which may also be incorporated as desired to ease pain which main be present) include, without limitation, benoxinate, benzocaine, bupivocaine, butamben, chloroprocaine, cocaine, diamocaine, dibucaine, dyclonine, ethyl chloride, etidocaine, euprocin, isobutamben, lidocaine, mepevicaine, oxethazine, pramoxine, prilocaine, pyrocaine, risocaine, rodocaine, tetracaine, and mixtures thereof; preferably benzocaine, lidocaine, tetracaine, and mixtures thereof);

(c) Clotting agents and clotting aids (when bandaging wounds and clotting is desired), which may include, without limitation,
  (i) physical agents that create barriers to blood flow such as petrolatum, gelatin film, KY Jelly;
  (ii) thickening agents which upon dissolution in serum, increase its viscosity so as to slow blood flow from the wound;
  (iii) agents which activate, supplement, or replace a component of the normally fully developed innate clotting cascade mechanism; and mixtures thereof;
and include, without limitation, antihemophilic factor, poliglusam, oxidized cellulose, thrombin, aminocaproic acid, ethamsylate, Factor II, Factor V, Factor VIIa, Factor VIII (recombinant forms available as Bioclate, Helixate FS, Kogenate FS, Recombinate and ReFacto), Factor IX (recombinant form available as BeneFix), Factor X, Factor XI, Factor XIa, Factor XII, Factor XIIa, Factor XIII, Factor XIIIa, prothrombin, vitamin K, gelatin film, oxsamarin, sulmarin, tranexamic acid, arachidonic acid, thromboxane $A_2$, inositol triphosphate, fibrinogen, high molecular weight kininogen, prekallihrein, RECOMTHROM THROMBIN, TOPICAL (RECOMBINANT), tissue factor, calcium, topical and local vasoconstrictors (such as, without limitation epinephrine), and nucleic acids (natural deoxy ribonucleic acid, ribonucleic acid, synthetic variants thereof, and analogs thereof, oligomers and polymers thereof, and modified versions thereof, etc) as disclosed in US 2007/0172432 (incorporated herein in its entirety by reference) and mixtures thereof.

A more complete list of compounds, most of which are pharmaceutical or veterinary, which can be utilized in the present invention includes, but is not limited to: abacavir, abamectin, abanoquil, abaperidone, abarelix, abecarnil, abiraterone, abitesartan, ablukast, abunidazole, acadesine, acamprosate, acaprazine, acebrochol, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutamide, acemetacin, aceneuramicacid, acenocoumarol, acepeprone, acepromazine, aceprometazine, acequinoline, acesulfame, acetaminosalol, acetanilide, acetarsone, acetaminophen, acetazolamide, acetiamine, acetiromate, acetohexamide, acetophenazone, acetophenetidin, acetorphine, acetosulfone, acetriozoic acid, acetylcysteine, acetyldigitoxin, acetyleucine, acetyltributyl citrate, acetyltriethyl citrate, acevaltrate, acexamin acid, acifran, acipimox, acitazanolast, acitemate, acitretin, acivicin, alcantate, aclarubicin, aclatonium napa-disilate, acolbifene, aconiazide, aconitine, acotiamide, acoxatrine, acreozast, acridorex, acriflavine, acrihellin, acrisorcin, acrivastine, acroinonide, acronine, actaplanin, actarit, Actiq®, actinoquinol, actisolide, actodigin, acyclovir, adafenoxate, adalimab, adamexine, adapalene, adaprolol, adatanserin, adefovir, adekalant, adelmidrol, ademitrionine, adenosine, adibendal, adicillin, adimolol, adinazolam, adiphenine, aditeren, aditoprim, adosopine, adozelesin, adrafinil, adrenalone, adrogolide, afalanine, afeletecan, afloqualone, afovirsen, afurolol, aganodine, aglepristone, agomelatine, aklomide, alacepril, alafosfalin, alagebrium, alamecin, alamifovir, alanine, alanosine, alaproclate, alatrofloxacin, alazanine triclofenate, albaconazole, albendazole, albuterol, albutoin, alclofenac, alclometasone, alcloxa, alcuronium, aldioxa, aldosterone, alemcinal, alendronic acid, alentemol, alepride, alestramustine, aletamine, alexidine, alexitol, alexomycin, alfacalcidol, alfadex, alfidalone, alfaprostol, alfatradiol, aldaxalone, alfentranil, alfuzosin, algeldrate, algestone, alibendol, aliconazole, alifedrine, alifurane, alilusem, alimadol, alinastine, alinidine, alipaminde, aliskiren, alitame, alitretinoin, alizapride, alletorphine, allobarbitol, allocamide, allocupreide, allomethadione, allopurinol, allylestrenol, allylprodine, almecillin, almestrone, alminoprofen, almitrine, almokalant, almotriptan, almoxatone, almurtide, alnespirone, alniditan, alonacic acid, alonimid, aloracetam, alosetron, alovudine, aloxidone, aloxiprin, aloxistatin, alozafone, alpertine, alphameprodine, alphamethadol, alphamethyldopa, alphaprodine, alpidem, alpiropride, alprafenone, alprazolam, alprenolol, alprenoxime, alprostadil, alrestatin, altanserin, altapizone, alteconazole, althiazide, altinicline, altoqualiine, altrenogast, altretamine, alvemeline, alverine, alvimopan, alvocidib, amadinone, amafalone, amanozine, amantadine, amantocillin, ambamustine, ambasilide, ambazone, ambenonium, ambenoxan, ambomycin, ambrisentan, ambroxol, ambruticin, ambucaine, ambucetamide, ambuphylline, ambuside, ambutonium, amcinafal, amcinafide, amcinonide, amdinocillin, amdoxovir, ambucort, amedalin, amelometasone, ameltolide, amelubant, amesergide, ametantrone, amethapred, amethocaine, amezapine, amezinium, amfenac, amfepentorex, amfetaminil, amflutizole, amfonelic, amicarbalide, amicloral, amicycline, anidantel, amidapsone, amidephrine, amiflamine, amifloverine, amifloxacin, amifostine, amiglumide, amikacin, amikhelline, amiloride, amiloxate, aminacrine, amindocate, amineptine, aminoglutethimide, aminohippuric acid, aminolevulinic acid, aminometradine, aminopentamide, aminophenazone, aminophylline, aminopromazine, aminopterin, aminopyrine, aminoquinol, aminoquinuride, a minorex, aminosalicylic acid, aminothiazole, amiodarone, amiperone, amphenazole, amipizone, amiprolose, amiquinsin, amisometradine, amisulprode, amiterol, amithiozone, amitivir, amitraz, amitriptyline, amitriptyinoxide, amixetrine, amlexanox, amlintide, amlodipine, amocarzine, amodiaquine, amolanone, amonafide, amoproxan, amopyroquine, amorolfine, amoscanate, amosulatol, amotosalen, amotriphene, amoxapine, amoxecaine, amoxicillin, amoxydramine, amperozide, anphechloral, amphenidone, amphetamine, amphomycin, amphotalide, amphotericin, ampicillin, ampiroxicam, amprenavir, amprolium, ampyrimine, ampyzine, amquinate, amrubicin, amsacrine, amtolmetin, amustaline, amylobarbital, angestone, anagrelide, anakinra, anaritide, anastrozole, anatibant, anaxirone, anazocine, anazolene, ancarolol, ancitabine, andolast, androstenediol, androstenedione, andulafungin, anecortave, anetholtrithion, angiotensin amide, andidoxamine, anidulafungin, anilamate, anileridine, anilopam, anipamil, aniracetam, anirolate, anisacril, anisindione, anisopirol, anisotropine, anisperimus, anitrazafen, anpirtoline, ansoxetine, antafenite, antazoline, antazonite, anthelmycin, anthralin, anthramycin, antipyrine, antrafenine, apadoline, apafant, apalcillin, apaxafylline, apaziquone, apazone, apicycline, aplindore, apomorphine, apovincamine, apraclonidine, apramycin, aprepitant, aprakalim, aprindine, aprinocarsine, apofene, aprosulate, aptazapine, aptiganel, aptocaine, aranidipine, aranotin, arbaprosil, arbekacin, arbutamine, arclofenin, ardacin, ardeparin, arecoline, arfalasin, arfendazam, arformoterol, argatroban, argimesna, argipressin, argiprestocin, arlidone, arimoclomol, aripiprazole, armodafinil, amolol, arofylline, artinolol, arprinocid, arpromidine, arsanilic acid, arteflene, artemether, artemisinin, artemotil, artenimol, artesunate, articaine, artilide, arundic acid, arzoxifene, ascorbic acid, arsenapine, aseripide, asimadoline, asobamast, asocainol, asoprisnil, aspartame, aspartocin, asperlin, aspirin, aspoxicillin, astemizole, astromicin, asulacrine, atamestane, ataprost, ataquimast, atazanavir, atenolol, atevirdine, atibeprone, atilmotin, atipamezole, atipromod, atiprosin, atizoram, atliprofen, atocalcitol, atolide, atomoxetine, atorvastatin, atosiban, atovaquone, atracurium, atrasentan, atraleuton, atrimustine, atrinositol, atromepane, atropine, atropine oxide, auranofin, aurothioglucose, avanafil, avasimibe, avicatonin, avalamycin, aviptadil, avitriptan, avizafone, avobenzone, azoparcin, avorelin, avridine, axamozide, axitirome, axomadol, azabon, azabuperone, azacitidine, azacitidine, azaclorzine, azaconazole, azacosrterol, azacyclonol, azaftozine, azalanstat, azalomycin, azaloxan, azamethiphos, azamethonium, azamulin, azanator, azanidazole, azaperohe, azapetine, azaquinzole, azaribine, azarole, azaserine, azasetron, azaspirium, azastene, azatadine, azathioprine, azelaic acid, azelastine, azelinnidipine, azepexole, azepindole, azetepa, azetirelin, azidamfenicol, azidocillin, azimexon, azimilide, azintamide, azipramide, azithromycin, azlocillin, azlocillin, azolimine, azosemide, aztomycin, aztreonam, azumolene, bacampicillin, bacitracin, baclofen, bacmecillinam, bakeprofen, balaglitazone, balazipone, balofloxacin, balsalazide, bamaluzole, bamaquimast, bambermycin, bambuterol, bamethan, bamifylline, bamipine, bamirastine, bamnidazole, banoxantrone, baquiloprim, barbexaclone, barbital, barixibat, barmastine, barnidipine, barucainide, barusiban, basifungin, batalbulin, batanopride, batebulast, batelapine, batilol, batimastat, batoprozine, baxitoizine, bazedoxifene, bazinaprine, becanthone, becatecarin, beciparcil, beclamide, beclapermin, becliconazole, beclobrate, beclomethasone, beclotiamine, befetupitant, befiperide, befloxatone, befunolol, befuraline, bekanamycin, belaperidone, belarizine, belfosdil, belotecan, beloxamide, beloxepin, bemarinone, bemegride, bemesetron, bemetizide, beminafil, bemiparin, bemetradine, bemoradan, bemotrizinol, benactyzine, benafentrine, benapryzine, benaxibine, benazepril, bencianol, bencisteine, benclonidine, bencyclane, bendacalol, bendamustine, bendazac, bendazol, benderizine, bendroflumethazide, benethamine penicillin, benexate, benfluorex, benfosformin, benfotiamine, benflurodil, benhepazone, benidipine, benmoxin, benolizime, benorilate, benorterone, benoxifos, benoxaprofen, benoxinate, benpenolisin, benperidol, benproperine, benrixate, bensalan, benserazide, bensuldazic acid, bentazepam, bentemazole, bentiamine, bentipimine, bentiromide, bentoquatam, benurestat, benzalkonium, benzarone, benzbromarone, benzestrol, benzethidine, benzethonium, benzetimide, benzilonium, benzindopyrine, benziodarone, benzmalecene, benznidazole, benzobarbital, benzocaine, benzoclidine, benzoctamine, benzodepa, benzododecinium, benzonatate, benzopyrronium, benzoquinonium, benzotript, benzoxiquine, benzoxonium, benzoylpas, benzphetamine, benzpiperylon, benzpyrinium, benzquercin, benzquinamide, benzthiazide, benztropine, benzydamine, benzylhydrochlorothiazide, benzylpenicillin, benzylsulfamide, bepafant, beperidium, bephenium, bepiastine, bepridil, beractant, beraprost, berberine, berefrine, bergenin, berlafenone, bermoprofen, bertosamil, berupipam, bervastatin, berythromycin, besigomsin, besipirdine, besonprodil, besulpamide, besunide, beta carotene, betacetylmethadol, betahistine, betaine, betameprodine, betamethadol, betamethasone, betamicin, betamipron, betaprodine, betaxolol, betazole, bethanacol, bethanidine, betiatide, betoxycaine, bevacizumab, bevantolol, bevonium, bexarotene, bexlosteride, bezafibrate, beztiramide, bialamicol, biapenem, bibezonium, bibrocathol, bicalutamide, bicifadine, bicoldil, biclofibrate, biclotymol, bicozamycin, bidimazium, bidisomide, bietamiverine, bietaserpine, bifemelane, bifepramide, bifeprofen, bifeprunox, bifluranol, bifonazole, bilastine, bimakalim, bimatoprost, bimoclomol, bimosiamose, bindarit, binedaline, binfloxacin, binfibrate, biniramycin, binizolast, binodenosine, binospirone, bioallethrin, botin, bipenamol, biperiden, biphenamine, biricodar, biriperone, bisacodyl, bisantrene, bisaramil, bisbendazole, bisbentiamine, bisbutiamine, bisdequilinium, bisfenazone, bisfentidine, bisnafide, bisorbin, bisoctriazole, bisoprolol, bisorcic, bisoxatin, bispyrithione, bithonol, bithionoloxide, butipazone, bitolterol, bitoscanate, bivalirudin, bizelesin, bleomycin, blonanserine, bluensomycin, bofumustine, bolandiol, bolasterone, bolazine, boldenone, bolenol, bolmantalate, bometolol, bopindolol, bomaprine, bornaprolol, borelone, borocaptane, bortezomib, bosentan, botiacrine, botulin toxin, boxidine, brallobarbital, brasofensine, brazergoline, brefonalol, bremazocine, brequinar, bretazenil, bretyllium, brifentanil, brimonidine, brinazaprone, brindoxime, brinzolamide, brivudine, brobactam, broclepride, brocrestine, brocrinat, brodimoprim, brofaromine, brofoxine, brolaconazole, brolamfetamine, bromadoline, bromamid, bromazepam, bromchlorenone, bromebric acid, bromerguride, brometenamine, bromfenac, bromhexene, bomindione, bromisovalum, bromociclen, bromocriptine, bromodiphenylhydramine, bromofenfos, bromofos, bromopride, bromoxanide, bromperidol, brompheniramine, broparestrol, broperamol, bropirimine, broquinaldol, brosotaminde, brostallicin, brosuximide, brotianide, brotizolam, brovanexine, brovincamine, broxaldine, broxaterol, broxitalamide, broxuridine, broxyquinoline, bucainide, bucetin, buciclovir, bucillamine, bucindolol, bucladesine, buclizine, buclosamide, bucloxic acid, bucolme, bucricaine, bucromarone, bucumolol, budesonide, budipine, budotitane, budralazine, bufenadrine, bufeniode, bufetolol, bufexamac, bufezolac, buflomedil, bufogentin, buformin, bufrolin, bufuralol, bufylline, bulaquine, bumadizone, bumecaine, bumepidil, bumetanide, bumetriazole, bunaftine, bunamidine, bunamiodyl, bunaprolast, bunazosin, bunitrolol, bunolol, buparvaquone, bupicomide, bupivacaine, bupranolol, buprenorphine, bupropion, buquinerin, buquinolate, buquiterine, buramate, burodiline, buserelin, buspirone, busulfan, butobarbital, butacaine, butacetin, butaclamol, butadiazamide, butafosfan, butalamine, butalbital, butamben, butamirate, butamisole, butamoxane, butanilicaine, butanserin, butantrone, butaperazine, butaprost, butaverine, butedronate, bytenafine, buterizine, butenamate, buthiazide, butibufen, butifrine, butikacin, butilfenin, butinazocine, butinoline, butirosin, butixirate, butixocort, butobendine, butoconazole, butocrolol, butoctamide, butofiolol, butonate, butopamine, butopiprine, butoprozine, butopyrammonium, butorphanol, butoxamine, butoxylate, butriptyline, butropium, butylscopolamine, butynamine, buzepide, cabastine, cabergoline, cactinomycin, cadralazine, cadrofloxacin, cafaminol, cafedrine, caffeine, calcifediol, calciprotriene, calcitriol, calcobutrol, caldaret, caldiamine, caloxetic acid, calteridol, clausterone, camazepam, cambendazole, camaglibose, camiverine, camptothecin and its analogues such as 9-amino camptothecin, 10-hydroxy camptothecin, 7-ethyl-10-hydroxy camptothecin, 9-nitro camptothecin and all other camptothecin analogues with six, seven and eight membered lactone rings, camonagrel, camostat, camylofin, canbisol, candesartan, candicidin, candocuronium, candoxatril, candoxatrilat, canertinib, canfosfamide, cangrelor, cannabinol, canrenoate, canrenone, capecitabine, capobenate, capobenic acid, capravirine, capreomycin, capromorelin, caproxamine, capsaicin, captamine, captodiame, captopril, capuride, carabersat, caracemide, carafiban, caramiphen, carbachol, carbadox, carbamazepine, carbentel, carbasone, carbaspirin, carbazeran, carbazochrome, carbazocine, cabenicillin, carbenoxolone, carbenzide, carbetapentane, carbetocin, carbidopa, carbimazole, carbinoxamine, carbiphene, carbofenotion, carboplatin, carboprost, carboquone, carbubarb, carburazepam, carbutamide, carbuterol, carcainium, carebastine, carfentanil, carfimate, cargutocin, cariporide, carisoprodol, carmantadine, carmofur, carmoterol, carmustine, camidazole, carnitine, carocainide, caroverine, caroxazone, carperidine, carperitide, carperone, carphenazine, carpindolol, carpipramine, carprazidil, carprofen, capronium, carsalam, carsatrin, cartasteine, cartazolate, carteolol, carubicin, carumonam, carvedilol, carvotroline, carzelesin, carzenide, casanthranol, casokefaminde, caspofungin, cathine, cathinone, cebaracetam, cedefingol, cefaclor, cefadroxil, cefalonium, cefaloram, cefamandole, cefaparole, cefatriazine, cefazaflur, cefazedone, cefazolin, cefbuperazone, cefanel, cefcapene, cefclidin, cefdaloxime, cefdinir, cefditoren, cefedrolor, cefempidone, cefepime, cefetamet, cefetecol, cefetriaole, cefivtril, cefixime, cefmatilen, cefmenoxine, cefinepidium, cefmetazole, ceminox, cefodizime, cefonicid, cefoperazone, ceforanide, cefoselis, cefotaxime, cefotetan, cefotiam, cefovecin, cefoxazole, cofoxitin, cefozopran, cefpimizole, cefpiramide, cefpodoxime, cefprozil, cefquinome, cefrotil, cefroxadine, cefsulodin, cefsumide, ceftazidime, cefteram, ceftezole, ceftibuten, ceftioflur, ceftiolene, ceftioxide, ceftioxime, ceftriaxone, cefuracetamime, cefuroxime, cefuzonam, celecoxib, celgosivir, celiprolol, cemadotin, cephacetrile, cephadrine, cephalexin, cephaloglycin. Cephaloridine, cephalothin, cephapirin, cepharanthine, cephradine, cericlamine, cerivastatin, ceronapril, ceruletide, cetaben, cetalkonium, cetamolol, cetefloxacin, cethexonium, cethromycin, cetiedil, cetilistat, cetirizine, cetocycline, cetopheincol, cetotiamine, cetoxime, cetraxate, cetrimonium, cetuximab, cetylpyridinium, cevimeline, chaulmosulfone, chenodiol, chinofon, chlofibrate, chlophendianol, chloracyzine, chloralose, chlorambusil, chloramines-T, chloramphenicol, chlorazanil, chlorbenoxamine, chlorbetamide, chlorcyclizine, chlordantoin, chlordiazepoxide, chlordimorine, chlorhexidine, chlorindanol, chlorisondamine, chloramadione, chlormerodrin, chlormezanone, chlormidazole, chlomaphazine, chloroazodin, chloroprednisone, chloroprocaine, chloropyramine, chloroquine, chloroserpidine, chlorothen, chlorothiazide, chlorotrianisene, chloroxine, chloroxylenol, chlorphenesin, chlorpheniramine, chlorphenoctium, chlorphenoxamine, chlorphentermine, chlorproethazine, chlorproguanil, chlorpromazine, chlorpropamide, chlorprothixene, chlorpyrifos, chlortetracycline, chlorthalidone, chlorthenoxazine, chlorzoxazone, cholecalciferol, cholesterol, choline, choline alfoscerate, chromic chloride, chromonar, ciadox, ciaftalan, ciamexon, cianergoline, cianidanol, cianopramine, ciapilome, ciaprost, ciarperone, ciclactate, ciclafrine, ciclazindol, ciclesonide, cicletanine, cicliomenol, ciclonicate, ciclonium, ciclopirox, ciclopramine, cicloprofen, cicloprolol, ciclosidomine, ciclosporin, ciclotizolam, ciclotropium, cicloxilic acid, cicloxolone, cicortonide, cidofovir, cidoxepin, cifenline, cifostodine, ciglitazone, ciheptolane, ciladopa, cilansertron, cilastatin, cilazapril, cilengitide, cilexin, cilnidipine, cilobamine, cilobradine, cilofungin, cilomilast, cilostamide, cilostazol, ciluprevir, cilutazoline, cimaterol, cimemoxin, cimetidine, cimetropium, cimicoxib, cimoxatone, cinacalcet, cinalukast, cinametic acid, cinamolol, cinanserin, cinaproxen, cinchophen, cinecromen, cinepazet, cinepazide, cinfenine, cinfenoac, cinflumide, cingestol, cinitapride, cinmetacin, cinnamaverine, cinnamedrine, cinnarizine, cinnofuradione, cinoctramide, cinodine, cinolazepam, cinoquidox, cinoxacin, cinoxate, cinoxolone, cinoxopazide, cinperene, cinprazole, cinpropazide, cinpromide, cintazone, cintriamide, cinuperone, cioteronel, cipamfylline, cipemastat, ciprafamide, cipralisant, ciprazafone, ciprefadol, ciprocinonide, ciprofibrate, ciprofloxacin, ciprokiren, cipropride, ciproquazone, ciprestene, ciramadol, cirazoline, cirolemycin, cisapride, cisatracurium, cinconazole, cismadinone, cisplatin, cistinexine, citalopram, citatepine, citenamide, citenazone, citicoline, citiolone, cizolirtine, cladribine, clamidoxic acid, clamikalant, clamoxyquin, clanfenur, clanobutin, clantifen, clarithromycin, clavulanate, clazolam, clazolimine, clazuril, clebopride, clefamide, clemastine, clemeprol, clemizole, clenbuterol, clenpirin, clentiazem, cletoquine, clevidipine, clevudine, clibucaine, clidafidine, clidanac, clindium, climazolam, climbazole, climiqualine, clinafloxacin, clindamycin, clinofibrate, clinolamide, clinprost, clioquinol, clioxanide, cliprofen, cliropamine, clobazam, clobenoside, clobenzepam, clobenorex, clobenztropine, clobetasol, clobetasone, clobutinol, clobuzarit, clocanfamide, clocapramine, clociguanil, clocinizine, clocortolone, clocoumarol, clodacaine, clodanolene, clodazon, clodoxopone, clodronate, clofarabine, clofazimine, clofenamic acid, clofeniclan, clofenetamine, clofenoxyde, clofevine, clofexamine, clofezone, clofibrate, clofibric acid, clofibride, clofilium, clofucarba, clofoctol, cloforex, clofurac, clogestone, cloguanamil, clomacrin, clomegestone, clometacin, clometherone, clomethiazole, clometocillin, clomifenoxide, clominorex, clomiphene, clomipramine, clomocycline, clomoxir, clonazepam, clonazoline, clonidine, clonitazine, clonixeril, clonixin, clopamide, clopenthixol, cloperastine, cloperidone, clopidogrel, clopidol, clopimozide, clopipazan, clopirac, cloponone, cloprendol, cloprostenol, cloprothiazole, cloquinate, cloquinozine, cloracetadol, cloranolol, clorazepate, clorazepic acid, clorethane, chlorexolone, clorfenvinos, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone, clotioxone, clotixamide, clotrimazole, clovoxamine, cloxacepride, cloxacillin, cloxazolam, cloxestradiol, cloximate, cloxotestosterone, cloxypendyl, cloxyquin, clozapine, co-amoxiclav, cobalamide, cocaine, codeine, codoxime, cofistatin, cogazocine, colchicines, colestolone, colfenamate, colforsin, colfosceril, colimecycline, colterol, coluracetam, conessine, congazone, conivaptan, conorphone, cormethasone, corticorelin, cortisone, cortisuzol, cortivazol, cortodoxone, cotinine, cotriptyline, coumaphos, coumazolin, coumermycin, coumetarol, creatinine, creatinolfosfate, cresotamide, cridanimod, crilvastin, crisnatol, crobenetine, croconazole, cromakalim, cromitrile, cromoglicate lisetil, cromolyn, crolom, cronidipine, cropropamide, crotamiton, crotetamide, crotoniazide, crotoxyfos, crufomate, cuprimyxin, cuproxoline, cyacetacide, cyamemazine, cyanocobalamine, cyclacillin, cyclamate, cyclamic acid, cyclandelate, cyclarbamate, cyclazocine, cyclazodone, cyclexanone, cyclindole, cycliramine, cyclizine, cyclobarbital, cyclobendazole, cycliramine, cyclobutoic acid, cyclobutyrol, cyclocumarol, cyclofenil, cycloguanil, cycloheximide, cyclomenol, cyclomethycaine, cyclopentamine, cyclopenthiazide, cyclopentolate, cyclophenazine, cyclophosphamide, cyclopregnol, cyclopyrronium, cycloserine, cyclothiazide, cyclovalone, cycotiamine, cycrimine, cyfluthrin, cyhalothrin, cyheptamide, cyheptropine, cynarine, cypenamine, cypermethrin, cypothrin, cyprazepam, cyprenorphine, cyprodenate, cyproheptadine, cyprolidol, cyproquinate, cyproterone, cyproximide, cyromazine, cysteamine, cysteine, cystine, cytarabine, cythiolate, dabelotine, dabigatran, dabuzalgron, dacarbazine, dacemazine, dacinostat, dacisteine, dacopafant, dactinomycin, dacuronium, dagapamil, dagluril, dalbavancin, dalbraminol, dalcotidine, daledalin, dalfopristin, dalteparin, daltroban, dalvastatin, dametralast, damotepine, danazol, daniquidone, danittracen, danofloxacin, danosteine, danthron, dantrolene, dapiprazole, dapitant, dapivirine, dapoxetine, dapsone, daptomycin, darbepoetin alpha, darbufelone, darenzepine, darglitazone, darifenacin, darodipine, darunavir, darusentan, dasantafil, dateliptium, daunorubicin, daxalipram, dazadrol, dazepinil, dazidamine, dazmegrel, dazolicine, dazopride, dazoquinast, dazoxiben, deboxament, debrisoquin, decamethonium, decimemide, decitabine, decitropine, declenperone, declopramide, decloxizine, decominol, decoquinate, dectaflur, deditonium, deferasirox, deferiprone, deferoxamine, deflazacort, defosfamine, defoslimod, degarelix, dehydroacetic acid, dehydrocholic acid, dehydroemetine, delanterone, delapril, delavirdine, delquamine, deergotrile, delfantrine, delfaprazine, selmadinone, delmetacin, delmpinol, delorazepam, deloxolone, delprostenate, delucemine, dembrexine, demecarium, demeclocycline, demecolcine, demecycline, demegestone, demelverine, demexiptiline, democonazole, demoxepam, demoxytocin, denatonium, denaverine, denbufylline, denipride, denofungin, denopamine, denotivir, denpidazone, denufosol, denzimol, depelestat, depramine, depreotide, deprodone, deprostil, deptropine, dequalinium, deracoxib, deramciclane, deriglidole, derpanicaine, dersalazine, desapidin, desciclovir, descinolone, deserpidine, desipramine, deeslanoside, desloratidine, deslorelin, desmeninol, desmethylmoramide, desmopressin, desocriptine, desogestrel, desmorphine, desonide, desoximetasone, desoxycorticosterone, desvenlafaxine, detajmium, detanosal, deterenol, detirelix, deticiclovir, detromidine, detorubicin, detrothyronine, devapamil, devazepide, dexamethasone, dexamisole, dexbrompheniramine, dexbudesonide, dexchlorpheniramine, dexclamol, dexecadotril, dexefaroxan, dexetimide, dexetozoline, dexfenfluramine, dexfosfoserine, dexibuprofen, deximafen, dexindoprofen, dexivacaine, dexketoprofen, dexlofexidine, dexloxiglumide, dexmedetomidine, dexmethylphenidate, dexnafenodonee, dexniguldipine, dexnorgestrel, dexormaplatin, dexoxadrol, dexpanthenol, dexpemedolac, dexpropranolol, dexproxibutene, dexrazoxane, dexsecoverine, dexsotalol, dextilidine, dextiopronin, dextofisopam, dextroamphetamine, dextrofemine, dextromethorphan, dextromoramide, dextrorphan, dextrothyroxine, dexcerapimil, sezaguanide, dezinamide, dezocine, diacerein, diacetamate, diacetolol, diamfenetide, diamocaine, diampromide, diamthiazole, diapamide, diarbarone, diathymosulfone, diatrizoate, diaveridine, diazepam, diaziquone, diazoxide, dibekacin, dibemethine, dibenzepin, dibenzothiophene, dibrompropamidine, bibromsalan, dibrospidium, dibucaine, dibuprol, dibupyrone, dibusadol, dicarbine, dicarfen, dichloralphenazone, dichloramine, dichlorisone, dichlormezanone, dichlorophen, dichlorphenarsine, dichloroxylenol, dichlorphenamide, dichlovos, diciferron, dicirenone, diclazuril, diclofenac, diclofenamide, diclofensine, diclofutrime, diclometide, diclonixin, dicloralurea, dicloxacillin, diclolinium, dicummol, dicyclomine, didanosine, didrovaltrate, dieldrin, dienestrol, dienogest, diethadione, diethylphthalate, diethylcarbamazine, dietylpropion, diethylstilbestrol, dethylthambutene, dietyltoluamide, dietifen, difebarbamate, difemerine, difemetorex, difenamizole, difencloxazine, difenoximide, difenoxin, difetarsone, difeterol, diflomotecan, diflorasone, difloxacin, difluanine, diflucortolone, diflumidone, diflunisal, difluprednate, diftalone, digitalis, digitoxin, digoxin, dihexyverine, dihydralazine, dihydrocodeine, dihydroergotamine, dihydrostreptomycin, dihydrotachysterol, diisobutylaminobenzoyloxypropyl theophylline, diisopromine, diisopropanolamine, diisopropylamine, dilazep, dilevalol, dilmefone, diloxanide, diltiazem, dimabefylline, dimadectin, dimecamine, dimeclonium, dimecrotic acid, dimefadane, dimefline, dimelazine, dimenhydrinate, dimenoxadol, dimepheptanol, dimepranol, dimepregnen, dimepropion, dimeprozan, dimesna, dimesone, dimetacrine, dimetamfetamine, dimethadione, dimethazan, dimethisoquin, dimethisterone, dimetholizine, dimethothizine, dimethoxanate, dimethylaminoethyl reserpilinate, dimethylthambutene, dimethyltubocurarinium, dimetipirium, dimetofrine, dimetridazole, diminazene, dimiracetam, dimoxamine, dimoxaprost, dimoxyline, dimpylate, dinaline, dinazafone, diniprofylline, dinitolmide, dinoprost, dinoprostone, dinsed, diohippuric acid, diosmin, diotyrosine, dioxadrol, dioxamate, dioxaphetyl butyrate, dioxation, dioxethedrin, dioxifedrine, dioxybenazone, dioxyline, dipenine, diperodon, diphemanil, diphenadione, diphenan, diphenchloxazine, diphenhydramine, diphenidol, diphenoxylate, diphenylpiperidinomethyldioxolan, diphenylpyraline, diphenoxazide, dipipanone, dipiproverine, dipivefrin, diprafenone, diprenorphine, diprobutine, diprofene, diprogulic acid, diproleandomycin, diprofylline, diproqualone, diproteverine, diprotrizoate, diproxadol, dipyridamole, dipyrithione, dipyrocetyl, dipyrone, diquafosol, dirithomycin, dirlotapide, disermolide, disquonium, disobutamide, sidofenin, sdisogluside, disopyramide, disoxaril, distigmine, disufenton, disulergine, disulfamide, disulfiram, disuprazoole, ditazole, ditekiren, ditercalinium, dithiaanine, ditiocade, ditiocarb, ditiomustane, ditolamide, ditophal, divabuterol, divalproex, divaplon, dixanthogen, dizatrifone, dizcilpine, dobesilate, dobupride, dobutamide, dobutamine, docarpamine, docebenone, docetaxel, doconazole, doconexent, docosanol, docusate, dodeclonium, dodicin, dofamium, dofequidar, dofetilide, dolasetron, doliracetam, domazoline, domiodol, domiphen, domipizone, domitroban, domoprednate, domoxin, domperidone, donepezil, donetidine, donitriptan, dopamantine, dopamine, dopexamine, dopropidil, doqualast, dorampimod, doramectin, doranidazole, dorastine, soreptide, doretinel, doripenem, dorzolamide. dosergoside, dosmalfate, dotarizine, dotefonium, dothiepin, doxacurium, doxapram, doxaprost, doxazosin, doxefazepam, doxenitoin, doxepine, doxergocalciferol, doxibetasol, doxifluridine, doxofylline, doxorubicin, doxpicomine, doxycycline, doxylamine, draflazine, dramedilol, draquinolo, drazidox, dribendazolew, drimidene, drobuline, drocinonide, droclidinium, drofenine, droloxifene, drometrizole, dromostanolone, dronabinol, drinedarone, dropempine, droperidol, droprenilamine, dropropizine, drospirenone, drotaverine, drotebanol, droxacin, droxicainide, droxicam, droxidopa, droxinavir, droxypropine, duazomycin, dulofibrate, duloxetine, dulozafone, dumorelin, dumetacin, duoperone, dupracetam, dutasteride, dyclonine, dyhydrogestrone, dymanthine, dyphylline, ebalzotan, ebastine, eberconazole, ebiratide, ebrotidine, ebselen, ecabapide, ecabet, ecadotril, ecalcidene, ecamsule, ecastolol, ecenofloxacin, echothiophate, ecipramidil, eclanamine, eclazolast, ecomustine, econazole, ecopipam, ecraprost, ectylurea, edaglitazone, edaravone, edatrexate, edelfosine, edetol, edifolone, edogestrone, edonentan, edotecarin, edotreotide, edoxudine, edratide, edronocaine, edrophonium, efaproxiral, efaroxan, efavirenz, efegatran, efepristin, efetozole, efletirizine, eflomithine, efloxate, eflucimibe, elfumast, efonidipine, efrotomycin, eganoprost, eglumetad, egtazic acid, equalen, elacridar, elantrine, elanzepine, elaarofiban, elbanizine, eldacimibe, eletriptan, elfazepam, elgotipine, elinafide, eliprodil, elisartan, ellagic acid, elliptinium, elmustine, elnadipine, elopiprazole, elsamitrucin, eltanolone, eltenac, eltoprazine, elucaine, elvucitabine, elzasonan, elziverine, emakalim, emapunil, embramine, embusartan, embutramide, emedastine, emepronium, emetine, emeglitate, emilium, emiteflur, emiverine, emodepside, emopamil, emorfazone, emtricitabine, emylcamate, enadoline, enalapril, enalaprilat, enalkiren, enazadrem, enbucrilate, encainide, enciprazine, enclomiphene, encyprate, endixaprine, endomide, endralazine, endryson, enecadin, enefexine, enestebol, enfenamic acid, enfluvirtide, englitazone, eniclobrate, enilconazole, enilospirone, eniluracil, eniporide, enisoprost, enloplatin, enocitabine, enofelast, enolicam, enoxacin, enoxamast, enoxaparin, enoximone, enoxolone, enipiprazole, enoxaprin, enpiroline, enprazepine, enprofylline, enpromate, enprostil, enramycin, enrasentan, enrofloxacin, ensacillin, ensulizole, entacapone, entecavir, entsufon, enviomycin, enviradene, enviroxime, enzacamene, anzastaurin, epalrestat, epanolol, eperezolid, eperisone, epervudine, ephedrine, epicainide, epicillin, epicriptine, epiestriol, epimestrol, epinastine, epinephrine, epinepheryl, epipropidine, epirizole, apioprim, epirubicin, epitetracycline, epithiazide, epitiostanol, eplerenone, elivanserin, epoprostenol, epostane, eprazinone, eprinomectin, epristeride, eprobemide, eprosartan, eprovafen, eproxindine, eprozinol, epsipranel, epaloprost, eptapirone, eptaplatin, eptastigmine, eptazocin, eptifibatide, equillin, erbulozole, erdosteine, ergocalciferol, ergonovine, ergotamine, eritoran, erizepine, erlotinib, ercainide, ersentilide, ertapenem, ertiprotafib, erythrityl tetranitrate, erythromycin, erythropoietin, esafloxacin, esaprazole, esatenolol, escitalopram, esculamine, eseridine, esflurbiprofen, esketamine, escarbazepine, esmolol, esomeprazole, esonarimod, esorubicin, esoxybutynin, espatropate, esproquin, estazolam, estradiol, estramustine, estrazinol, estriol, estrofurate, estrogens, estrone, estropipaten esupone, eszopiclone, etabenzarone, etacepride, etafedrine, etafenone, etalocib, etamestrol, etaminile, etamiphylline, etamocycline, etanercept, etanidazole, etanterol, etaqualone, etarotene, etasuline, etazepine, etazolate, etebenecid, eterobarb, etersalate, ethacridine, ethacrynic acid, ehtambutol, ethamivan, ethamsylate, ethaverine, ethenzameide, ethiazide, ethinamate, ethinyl estradiol, ethionamide, ethisterone, ethoheptazine, ethomoxane, ethonam, ethopabate, ethopropazine, ethosuximide, ethotoin, ethoxazene, ethoxazorutoside, ethoxzolamide, ethybenztropine, ethyl biscoumacetate, ethyl carfluzepate, ethyl cartrizoate, ethyl dibunate, ethyl dirazepate, ethyl loflazepate, ethylestrenol, ethylhydrocupreine, ethylmethylthiambutene, ethylmorphine, ethylnorepinepherine, ethylstilbamine, ethylnerone, ethylnodil, ethypicone, etibendazole, eticlopride, eticyclidine, etidocaine, etidronate, etidronic acid, etifelmine, etifenin, etifoxine, etilamfetamine, etilefrine, etilevodopa, etinidine, etipirium, etiprendol, etiproston, etiracetam, etiroxate, etisazole, etisomicin, etisulergine, etizolam, etocarlide, etocrylene, etodolac, etodroxizine, etofamide, etofenamate, etofenprox, etofibrate, etofermin, etofuradine, etofylline, etoglucid, eorolex, etolotifen, etoloxamine, etomidate, etomidoline, etomoxir, etomitazene, etonogestrel, etoperidone, etoposide, etoprindole, etoprine, etoricoxib, etorphine, etosalamide, etoxadrol, etoxeridine, etozolin, etrabamine, etravirine, etretinate, etriciguat, etryptamine, etymemazine, eucaine, eucalyptol, eugenol, euprocin, evandamine, evemirnmicin, everolimus, evicromil, exalamide, exanetazime, examorelin, exaprolol, exatecan, exemestane, exenatide, exepanol, exifone, exiprofen, exisulind, ezetimibe, ezlopitant, factor VII (such as NovoSeven®), fadolmidine, fadrozole, falecalcitriol, falintolol, falipamil, falnidamol, famciclovir, famirapinium, famotidine, famotine, fampridine, famprofazone, fampronil, fananserin, fanapanel, fandofloxacin, fandosentan, fanetizole, fantofarone, fantridone, farglitazar, fasidotril, fasiplon, fasoracetam, faudil, fazadinium, fazarabine, febantel, febarbamate, febuprol, febuverine, febuxostat, feclemine, feclobuzone, fedotozine, fedrilate, felbamate, felbinac, felipyrine, felodipine, feloprentan, felypressin, femoxetine, fenabutene, fenacetinol, fenaclon, fenadiazole, fenaftic acid, fenalamide, femalcomine, fenamifuril, fenamole, fenaperone, fenbendazole, fenbenicillin, fenbufen, fenbutreazate, fencamfamin, fencibutirol, fenclexonium, fleclofenac, fenclonine, fenclorac, fenclozic acid, fendiline, fendizoate, fendosal, feneritrol, fenestrel, fenethazine, fenethylline, fenetradil, fenflumizole, fenfluramine, flenfluthrin, fengabine, fenharmane, fenimide, feniodium, fenipentol, fenirfibrate, fenisorex, fenitrothion, fenleuton, fenmetozole, fenmetraminde, fenobam, fenocinol, fenocitimine, fenofibrate, fenoldopam, fenoprofen, fenoterol, fenoerine, fenoxazoline, fenoxedil, fenozolone, fenpentadiol, fenperate, fenprpalone, fenpipramide, fenpiprane, fenpiverinium, fenprinast, fenproporex, fenprostalene, fenquiaone, fenretinide, fenspiride, fentanyl, fenthion, fentiazac, fenticlor, fenticonazolem, fentonium, fenvalerate, fenyripol, fepentolic acid, fepitrizol, fepradinol, feprazone, fepromide, feprosidnine, ferpifosate, fesoterodine, fetoxylate, fexicaine, fexinidazole, fexofenadine, fezatione, fezolamine, fiacitabine, fialuridine, fibracillin, fidarestat, fidexaban, fiduxosin, figopitant, filaminast, filenadol, filipin, filgrastim, finafloxacin, finasteride, fingolimod, fipamezole, fipexide, fipronil, firocoxib, flavamine, flavodic acid, flavodilol, flavoxate, flazalone, flecainide, flerobuterol, fleroxacin, flesinoxan, flestolol, fletazepam, flezelastine, flibanserin, flindokalner, flocalcitriol, floctafenine, flomoxef, floptopione, florantyrone, flordipine, floredil, florfenicol, florifenine, flosatidil, flosequinan, flosulide, flotrenizine, floverine, floxacillin, floxacrine, floxuridine, flucizine, flualamine, fluanisone, fluazacort, fluazuron, flubanilate, flubendazole, flubepride, flucarbril, flucetorex, flucindole, flucinprazine, flucloronide, fluconazole, flucrylate, flucytosine, fludalanine, fludarabine, fludazonium, fludeoxyglucose, fludiazepam, fludorex, fludoxopone, fludrocortisone, flufenamic acid, flufenisal, flufosal, flufylline, fugestone, fluindarol, fluindione, flumazenil, flimecinol, flumedroxone, flumequine, flumeridone, flumethasone, flumethiazole, flumetramide, flumexadol, flumezapine, fluminorex, flumizole, lfumoxonide, flunamine, flunarizine, flunidazole, flunisolide, flunitrazepam, flunixin, flunoprost, flunoxaprofen, fluocinolone, fluocinonide, fluocortin butyl, fluocortolone, fluorescein, fluoresone, fluorodopa, fluorometholone, fluorosalan, fluorouracil, fluotracen, fluoxetine, fluoxymesterone, fluparoxan, flupentixol, fluperamide, fluperlapine, fluperolone, flupheazine, flupimazine, flupirtine, flupranone, fluprazine, fluprednidene, fluprednisolone, flupofen, fluprofylline, fluproquazone, fluprostenol, fluquazone, fluradoline, flurandrenolide, flurantel, flurazepam, flurbiprofen, fluretofen, flurithromycin, flurocitabine, flurofamide, flurogestone, flusoxolol, fluspiperone, fluspirilene, fluticasone, flutamide, flutazolam, flutemazepam, flutiazin, fluticasone, flutizenol, flutomidate, flutonidine, flutoprazepam, flutrimazole, flutroline, flutropium, fluvastatin, fluvoxamine, fluzinamide, fluzoperine, fodipir, folic acid, follitropin alpha, follitropin beta, fomepizole, fomidacillin, fominoben, fomiversen, fomocaine, fonazine, fondaparinux, fopirtoline, forasartan, forfenimex, formebolone, formestane, formetorex, forminitrazole, formocortal, formoterol, forodesine, foropafant, fosamprenavir, fosarilate, fosazepam, fosenazide, fosfluconazole, fosfocreatinine, fosfomycin, fosfonet, fosfosal, fosfructose, fosinopril, fosinoprilat, fosmenic acid, fosmidomycin, fosopamine, fosphenytoin, fospirate, fosquidone, fostedil, fosrtriecin, fosveset, fotemustine, fortrenamine, fozivudine, frabuprofen, fradafiban, frakefamide, framycetin, frentizole, freselestat, fronepidil, fropenem, frovatriptan, froxiprost, ftaxilide, ftivazide, ftormetazine, ftorpropazine, fubrogonium, fudosteine, fuladectin, fulvestrant, fumagillin, fumoxicillin, fungimycin, fuprazole, furacrinic acid, furafylline, furalazine, furaltadone, furaprofen, furazabol, furazolidone, furazolium, furbicillin, furcloprofen, furegrelate, furethidine, furfenorex, furidarone, furmethoxadone, furnidipine, furobufen, furodazole, furofenac, furomazine, furomine, furosemide, furostilbestrol, fursalan, fursultiamine, furtherene, furtrethonium, fusafungine, fusidate, fusidic acid, fuzlocillin, gabapentin, gabapexate, gaboxadol, gacyclidine, gadobenate; gadobutrol, gadocolectic acid, gadodiamine, gadofosveset, gadomelitol, gadopenamide, gadopentetate, gadoteric acid, gadoteridol, gadoversetamide, gadoxetate, gadoxeticaicid, galamustine, galntamine, galarubicin, galasomite, galdansetron, gallamine triethiodide, gallopamil, galocitabine, galosemide, galtifenin, gamfexine, gamolenic acid, gamaxolone, ganciclovir, ganefromycin, ganglefene, ganstigmine, gantacurium, gantofiban, gapicomine, gapromidine, garenoxacin, gatifloxacin, gavestinel, geclosporin, gedocarnil, gefarnate, gefitinib, gemazocine, gemcabene, gemcadiol, gemcitabine, gemeprost, genfibtrozil, gemifloxacin, gemopatrilat, gentamicin, gepefrine, gepirone, geroquinol, gestaclone, gestadienol, gestodene, gestonorone, gestrinone, gevotroline, gimatecan, gimeracil, giparmen, giracodazole, giractide, girisopam, gitaloxin, gitoformate, glafenine, glaspimod, glatiramer acetate. glemanserin, glenvastatin, gliamilide, glibotnuride, glibutimine, glicaramide, glicetanide, gliclazide, glicondamine, glidazamide, gliflumide, glimepiride, glipalamide, glipizide, gliquidone, glisamuride, glisentide, glisindamine, glisolamide, glisoxepide, gloxazone, gloximonam, glucametacin, glucosamine, gluronolactone, glucuronamide, glunicate, glyburide, glybuthiazole, glubuzole, glycopyrrolate, glycylamide, glyhexamide, glymidine, glyoctamide, glyparamide, glypinamide, glyprothiazole, glysobuzole, goralatide, goserelin, gramicidin, granisetron, grepafloxacin, griseofulvin, guabenxan, guacetisal, guafecainol, guaiactamine, guaiapate, guaietolin, guaifenesin, guaimesal, guaisteine, guaithylline, guanabenz, guanacline, guanadrel, guanazodine, guanclofine, guancydine, guanethidine, guanfacine, guanisoquin, guanoclor, guanoctine, guanoxabenz, guanoxan, guanoxyfen, gusperimus, halazepam, halazone, halcinonide, halethazole, halobetasol, halocortolone, halofantrine, halofenate, halofuginone, halometasone, halonamine, halopemide, halopenium, haloperidol, halopredone, haloprogesterone, haloprogin, haloxazolam, haloxon, haloqionol, hamycin, hedaquinium, heliomycin, hepronicate, heptabarbital, heptaverine, heptolamide, hepzidine, heroin, hetacillin, hetaflur, heteronium, hexachlorophene, hexacyclonate, hexacyprone, hexadiline, hexafluorenium, hexamethonium, hexaminolevulinate, hexapradol, hexaprofen, hexapropymate, hexasonium, hexazole, hexedine, hexestrol, hexetidine, hexobarbital, hexobendine, hexocyclium, hexoprenaline, hexopyrronium, heylcaine, histamine, histapyrrodine, histidine, homarylamine, homatropine, homidium, homochlorcyclizine, homofenazine, homopipramol, homosalate, homprenorphine, hopantenic acid, hoquizil, human growth hormone, Humalin®, Humalog®, human papilloma quadrivalent types 6,11,16,18, hycanthone, hydracarbazine, hydralazine, hydragaphen, hydrobentizide, hydrochlorothiazide, hydrocodone, hydrocortisone, hydroflumethiazide, hydromadinone, hydromorphinol, hydromorphone, hydroquinone, hydroxyindasate, hydroxyindasol, hydroxocobalamin, hydroxyamphetamine, hydroxychloroquin, hydroxydione, hydroxypethidine, hydroxyphenamate, hydroxyprocaine, hydroxyprogesterone, hydroxypyridine tartrate, hydroxystenozole, hydroxystilbamidine, hydroxytetracaine, hydroxyzine, hymecromone, hyoscyamine, ibafloxacin, ibandronate, ibazocine, ibopamine, ibrolipim, ibrotamide, ibudalast, ibufenac, ibuprofen, ibuproxam, ibutamoren, ibuterol, ibutilide, ibuverine, icaridin, icatibant, iclaprim, icazepam, icodulinium, icofungipen, ifometasone, icopezil, icosapent, icospiramide, icotidine, icrocaptide, idarubicin, idaverine, idazoxan, idebenone, idenast, idoxifene, idoxuridine, idralfidine, idramantone, idraparinux, idrapril, idremcinal, idrociliamide, idronoxil, idropranolol, iferanserin, ifetroban, ifosfamide, ifoxetine, iganidipine, igmesine, iguratimod, ilaprazole, ilatreotide, ilepcimide, iliparcil, ilmofosine, iloomastat, ilonidap, iloperidone, imafen, imanixil, imatinib, imazodan, imcarbofos, imiclopazine, imidafenacin, imidapril, imidaprilat, imidocarb, imidoline, imidurea, imiglitazar, imiglucerase, imiloxan, iminophenimide, imipenem, imipramine, imipraminoxide, imiquimod, imirestat, imitrodast, imolamine, imoxiterol, impacarzine, implitapide, impromidine, improsulfan, imuracetam, inamirone, inaperisone, incadronic acid, indacaterol, indacrinone, indalpine, indanazoline, indanidine, indanorex, indapamide, indatraline, indecainide, indeloxazine, indenolol, indibulin, indigotindisulfonate, indinavir, indiplon, indisetron, indobufen, indocate, indocyanine green, indolapril, indolidan, indomethacin, indopanolol, indopine, indoprofen, indoramin, indorenate, indoxole, indriline, inecalcitol, Infanrix®, infliximab, ingliforib, inicarone, inocterone acetate, inogatran, inosine, inositol, improquoone, interferon beta-1a, interferon betalb, intoplicine, intrazole, intriptyline, insulin, insulin analog, inulin, iobenguane, iobenzamic acid, iobitridol, iobutoic acid, icanlidic acid, iocarmic acid, iocetamic acid, iodamine, iodipamide, iodixanol, iodoantipyrine, iodocholesterol, iodohippurate, iodoquinol, iodothiouracil, idoxamic acid, iofetamine, ioflupane, iofratol, ioglicic acid, ioglucol, ioglunide, ioglycamic acid, iogulaamide, iohexol, iolidonic acid, iolixanic acid, iolopride, iomazenil, iomeglamic acid, iomeprol, iomethin, iometopane, iomorinic acid, iopamidol, iopanoic acid, iopentol, iophendylate, iophenoxic acid, iopromide, iopronic acid, iopydol, iopydone, iosarcol, isofenamic acid, ioseric acid, iosimenol, iosimide, iosulamide, iosumetic acid, iotasul, ioteric acid, iothalamate, iothalmic acid, iotranic acid, iotriside, iotrizoic acid, iotrolan, iotroxic acid, iotyrosine, iovesol, ioxabrolic acid, ioxaglic acid, ioxilan, ioxitalamic acid, ioxotrizoic acid, iozomic acid, ipamorelin, ipazilide, ipenoxazone, ipexidine, ipidacrine, ipodate, iprgratine, ipramidil, ipratropium, ipravacaine, iprazochrome, ipriflavone, iprindole, ipocinidine, iproclozide, iprocrodol, iprofenin, iproheptine, iproniazide, ipronidazole, iproplatin, iprotiazem, iproxamine, iprozilamine, ipsalazide, ipsapirone, iquindamine, iralukast, irampanel, irbesartan, irindalone, irinotecan, irloxacin, irofulven, irolapride, iroxanadine, irsogladine, irtemazole, isalidole, isalsteine, isamfazone, isamoltan, isamoxole, isatoribine, isaxonine, isbogrel, isbufylline, ispamicin, isoamilinile, isobromindione, isobucaine, isobutamben, isocarboxazid, isoconazole, isocromil, isoetharine, isoflupredone, isoflurophate, isomazole, isomazole, isomerol, isometamidium, isomethadone, isomethoheptene, isomolpan, isoamylamine, isoniazid, isonixin, isoprazole, isoprednidene, isoprofen, isopropamide, isopropicillin, isoproterenol, isosrbide, isospaglumic acid, isosulfan blue, isosulpride, isothipendyl, isotiquimide, isotretinoin, isoxaprolol, isoxepac, isoxicam, isoxsuprine, isradipine, israpafant, istrdefylline, itameline, itanoxone, itasetron, itazigrel, itopride, itraconazole, itriglumide, itrocainide, itrocinonide, iturelix, ivbradine, ivarimod, ivermectin, ivoqualine, ixabepilone, izonsteride, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, labradimil, lachesine, lacidipine, lacosamide, lactalfate, lactilol, lactulose, ladirubicin, ladostigil, laflunimus, lafutine, laidlomycin propionate, lamifiban, lamivudine, lamotrigine, lamitidine, lanatoside, landiolol, lanepitant, lanicemine, laniquidar, lanoconazole, lanperisone, lanproston, lanreotide, lansoprazole, lantusg, lapatinib, lapisteride, laprafylline, lapyrium, laquinimod, lasalocid, lasinavir, lasofoxifene, latanoprost, laudexium, laurcetium, laurocapram, lauroguadine, laurolinium, lauryl isoquinolinium, lavoltidine, lazabemide, lecimibide, ledazerol, ledoxantrone, lefetamine, leflunomide, lefradafiban, leiopyrrole, lemidosul, lemidipine, leminoprazole, lemoxinol, lemuteporfin, lanalidomine, lenampicillin, lenapenem, leniquisin, leuperone, leptacline, lercanidipine, lergotrile, lerisetron, lesoptiron, lestaurtinib, leteprinim, leteprinim, letimide, letosteine, letrazuril, letrozole, leucinocaine, leucocianidol, leucovorin, leuprolide, leurubicin, levalbuterol, levallorphan, levamfetamine, levamisole, levcromakalim, levcycloserine, levdobutamine, levemoamil, levetiracetam, levisoprenaline, levlofexidine, levmetamfetamine, levobetaxolol, levobunolol, levobupiacaine, levocabastine, levocamitine, levodopa, levodropropizine, levofacetoperane, levofenfluramine, levofloxacin, levofluraltadone, levoleucovorin, levomenol, levomepromazine, levomethadone, levomethadyl acetate, levomethorphan, levometiomeprazine, levomoprolol, levomoramide, levonantradol, levonordefrin, levonorgestrel, levophenacylmorphan, levopropoxyphene, levopropylcilline, levopropuylhexedrine, levoprotiline, levorin, levormeloxifene, levorphanol, levosalbutamol, levosemotiadil, levosimendan, levosulpiride, levothyroxine, levotofisopam, levoxadrol, lexipafant, lexithromycin, lexofenac, liarozole, libecillide, libenzapril, licarbazepine, licofelone, licostinel, lidadronic acid, lidamine, lidanserin, lidocaine, lidoferin, lidorestat, lifariaine, lifibrate, lifibrol, lilopristone, limaprost, limazocic acid, linarotene, lincomycin, lindane, linetastine, linezolid, linogliride, linopirdine, linotroban, lisinidomine, lintitript, lintopride, liothyronine, lipoic acid, liraglutide, liranaftate, lirequinil, lirexapride, lirimilast, liroldine, lisadimate, lisinopril, lisofylline, lisuride, litomeglovir, litoxetine, litracen, lividomycin, lixazinone, lixivaptan, lobapolatin, lobeline, lobendazole, lobenzarit, lobucavir, lobuprofen, locicortolone, lodaxaprine, lodazecar, lodelaben, lodenosine, lodinixil, lodiperone, lodoxamide, lofemizole, lofendazam, lofentanil, lofepramine, lofexidine, loflucarban, lombazole, lomefloxacin, lomeguarib, lomerizine, lometraline, lometrexol, lomevactone, lomifylline, lomofungin, lomustine, lonafamib, lonapalene, lonaprofen, lonazolac, lonidamine, loperamide, lopinavir, lopirazepam, lopobutan, loprazolam, loracarbef, lorajmine, lorapride, loratadine, lorazepam, lorbamate, lorcainide, lorcinadol, loreclezole, lorglumide, lormetazepam, lomoxicam, lopiprazole, lortalamine, lorzafone, losartan, losigamone, losindole, losmiprofen, losoxantrone, losulazine, loteprednol, lotrafiban, lotrifen, lotucaine, lovastatin, loviride, loxanast, loxapine, loxiglumide, loxoprofen, loxoribine, lozilurea, lubazodone, lubeluzole, lubiprostone, lucanthone, lucartamide, lucimycin, lufenuron, lufironil, lufuradom, luliconazole, lumiracoxib, lupitidine, luprostiol, lurasidone, lurosetron, lurototecan, lusaperidone, luxabendazole, lydimycin, lymecycline, lynestrenol, lypressin, mabuprofen, mabuterol, maduramicin, mafenide, mafoprazine, mafosfamide, malathion, maleylsulfathiazole, malotilate, mangafodipir, manidipine, manifaxine, mannomustine, manozodil, mantabegron, mapinastine, maprotiline, maraviroc, marbofloxacin, maribavir, maridomycin, marimastat, mariptiline, maropitant, maroxepin, masoprocol, maxacalcitol, maytansine, mazapertine, mazaticol, mazindol, mazipredone, mazokalim, mebanazine, mebendazole, menbenoside, mebeverine, mebezonium, mebhydrolin, mebiquine, mebolazine, mebrofenin, mebutamate, mebutizide, mecamylamine, mecarbinate, mecetronium, meciadanil, mecinarone, meclinertant, meclizine, meclocycline, meclofenamaic acid, meclofenoxate, meclonazepam, mecloqualone, meclorisone dibutyrate, mecloxamine, mecobalamin, medazepam, medazomide, medetomidine, medibazine, medifoxamine, medorinone, medorubicin, medrogestrone, medronic acid, medroxalol, medroxyprogesterone acetate, medrylamine, medrysone, mefeclorazine, mefenamic acid, mefenidil, mefenidramium, mefenorex, mefeserpine, mefexamide, mefloquine, mefruside, megalomyciin, megestrol, megace, meglitinide, meglucycline, meglumine, meglutol, meladrizine, melagatran, melarsomine, melarsonyl, melarsoprol, meldonium, melengestrol acetate, meletimide, melevodopa, melinamide, melitracen, melizame, meloxicam, melperone, melphalan, melquinast, meluadrine, memantine, memotine, menabitan, menadiol, menadione, menadoxime, menatetrenone, menbutone, menfegol, menglytate, menitrazepam, menoctone, menogaril, menobentine, mepazine, mepenzolate, meperidine, mephenesin, mephenoxalone, mephentermine, mephenytoin, mephobarbital, mebaral, mepindolol, mepiperphenidol, mepiprazole, mepiroxol, mepitiostane, mepivacaine, mepixanox, mepramidil, meprednisone, meprobamate, meprochol, meproscillarin, meprotixol, meprylcaine, meptazinol, mequidox, mequinol, mequitamium, mequitazine, meradimqate, menthyl anthranilate, merafloxacin, meralein, meralluride, merbaphen, merbromin, mercaptomerin, mercaptopurine, mercuderamide, mercufenol, mercumatilin, mergocriptine, meribendan, merimepodib, meropenem, mersalyl, mertialide, mesabolone, mesalamine, meseclazone, mesocarb, mesoridazine, mesipiperone, mespirenone, mestanolone, mesterolone, mestranol, mesudipine, mesulergine, mesulfamide, mesulfen, mesuprine, metabromsalan, metbutethamine, metabutoxycaine, metacetamol, metaclazepam, metacresol, metaglycodol, metahexamide, metalkonium, metalol, metamelfalan, metamfazone, metamfenpramone, metampicillin, metanixin, metapramine, metaproterenol, metaraminol, metaxalone, metazamide, metazide, matazocine, metbufen, meteneprost, metergoline, metergotamine, metescufylline, metesculetol, metesind, metethoheptazine, metformin, methacholine, methacycline, methadone, methadyl acetate, methallenestril, methallibure, methalthiazide, methamphetamine, methandriol, methandrostenolone, methaniazide, methantheline, methaphenilene, methapyrilene, methaqualone, metharbital, methastyridone, methazolamide, methdilazine, methenamine, methenolone, metheptazine, methestrol, methetoin, methikcillin, mthimazole, methiodal, methiomeprazine, methionine, methisazone, methitural, methixene, methocarbamol, methocidin, methohexital, methopholone, methoprene, methoserpidine, methotrexate, methotrimeprazine, methoxamine, methoxsalen, methoxyphedrine, methoxyphenamine, methoxypromazine, methscopolamine, methsuximide, methyclothiazide, methyl aminolevulinate, methyl palmoxirate, methyl salicylate, methylatropine, methylbenactyzium, methylbenzethonium, methylcromone, methyldesorphine, methyldihydromorphine, methyldopa, methylene blie, methylephedrine, methylergometrine, methylergonovine, methyllparaben, methylphenidate, methylprednisolone, methyltestosterone, methylthiouracil, methynodiol, methyprylon, methysergide, metiamide, metiapine, metiazinic acid, metibride, meticrane, metildigoxin, metindizate, metioprim, metioxate, metipirox, metiprenaline, metitepine, metizoline, metkephamid, metochalcone, metocinium, metoclopramide, metocurine, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoate, metronidiazole, meturedepa, metyrapone, metyrosine, mevastatin, mexafylline, mexazolam, mexenone, mexiletine, mexiprosil, mexoprofen, mexrenoate, mezacopride, mezepine, mezilamine, mezlocillin, miaanserin, mibefradil, mibolerone, miboplatin, micafungin, miconazole, micronomicin, midaflur, midafotel, midaglizole, midamaline, midaxifylline, midazogrel, midazolam, midecamycin, midestein, midodrine, midostaurin, mifentidine, mifepristone, mifobate, iglitol, miglustat, mikamycin, milacainide, milacemide, milameline, milataxel, milenperone, milfasartan, milipertine, miloxacin, milrinone, miltefosine, milverine, mimbane, minalrestat, minamestane, minaprine, minaxolone, mindodilol, mindoperone, minepentate, minocromil, minocycline, minodronic acid, minopafant, minoxidil, mioflaazine, mipitroban, mipragoside, miproxifene, mirfentanil, mirincamycin, miripirium, miriplatin, mirisetron, miristalkonium, miroprofen, mirosamicin, mirostipen, mirtazapine, misonidazole, misoprostol, mitemcinal, mitiglinide, mitindomine, mitobronitol, mitocarcin, mitoclomine, mitocromin, mitoflaxone, mitogillin, mitoguazone, mitolactol, mitomalcin, mitomycin, mitonafide, mitopodozide, mitoquidone, mitosper, mitolane, mitotenamine, mitoxantrone, mitozolomide, mitradipide, mivacurium, mivobulin, mivotilate, mixidine, mizolastine, mizoribine, mobecarb, mobenzoxamine, mocimycin, mociprazine, moclonemide, moctamide, modafinil, modaline, modecainide, modipafant, moexipril, moexiprilat, mofarotene, mofebtazone, mofegiline, mofezolac, mofloverine, mofoxine, mofuisteine, molfarnate, molinazone, molindone, molracetam, molsidomine, mometasone, monalazone, monatepil, monesin, monobenzone, monoctanoin, monometacrine, monophosphothiamine, monoxerutin, montelukast, monterelin, moperone, mopidamol, mopidralazine, moprolol, moquizone, morantel, morazone, morclofone, morforex, moricizine, morinamide, morniflumate, morocromen, moroxydine, morpheridine, morphine, morsuximide, mosapramine, mosapride, motapizone, motexafin, motrazepam, motrtinide, moveltipril, moxadolen, moxalactam, moxaprindine, moxastine, moxaverine, moxazocine, moxestrol, moxicoumone, moxidectin, moxifloxacin, moxilubant, moxipraquine, moxirapine, moxisylate, moxnidazole, moxonidine, mozavaptan, mozenavir, mubritnib, mupirocin, murabutide, muraglitazar, mureletecan, murocainide, muzolimine, mycophenolic acid, mycophenolate mofetil, myfadol, myrophine, myrtecaine, nabazenil, nabilone, nabitan, naboctate, nabumetone, nacartocin, nadide, nadiofloxacin, nadolol, nadoxolol, nafagrel, nafamostat, nafarelin, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypamide, naglivan, nalbuphine, nalfurafine, nalidixic acid, nalmefene, nalmexone, nalorphine, naloxone, naltrexone, naminidil, anminterol, namirotene, namoxyrate, nanafrocin, nandrolone, nanterinone, nantradol, napactadine, napamezole, naphazaoline, naphthonone, napirimus, napitane, naproxime, naproxen, naproxol, napsagatran, naranol, barasin, naratriptan, nardetoterol, naroparcil, natamycin, nateglinide, navuridine, naxagolide, naxaprosteine, naxifylline, nealbarbital, nebantan, nebidrazine, nebivolol, neboglamine, nebracetam, nebramycin, necopidem, nedaplatin, nedocromil, nefazodone, nefiracetam, neflumozide, nefopam, nelarabine, neldazosin, nelezaprine, nelfinavir, neltenexine, nelzarabine, nemadectin, nemazoline, nemifitide, nemonapride, nemonoxacin, nemorubicin, neocinchophen, neomycin, neostigmine, nepadutant, nepafenac, nepaprazole, nepicastat, nepinalone, nequinate, neramexane, neraminol, nerbacadol, neridronic acid, nerisopam, nesapidil, nesiritide, nesosteine, nestifylline, neticonazole, netilmicin, netivudine, netobimin, netoglitazone, netupitant, neutramycin, neviparine, nexeridine, nexopamil, niacin, niacinamide, nialamide, niaprazine, nibroxane, nicafenine, nicainoprol, nicametane, nicanartine, nicaraven, nicarbazin, nicardipine, nicergoline, niceritol, niceverine, niclofolan, niclosamide, nicoboxil, nicoclonate, nicocodine, nicocortonide, nicocidodine, nicoduozide, nicofibrate, nicofuranose, nifurate, nicogrelate, nicomol, nicomorphine, nicopholine, nicoracetam, nicorandil, nicothiazone, nicotredole, nicoxamat, nictiazem, nictindole, nidroxyzone, nifedipine, nifekalant, nifenalol, nifenazone, niflumic acid, nifungin, nifuradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifurprazine, nifurquinazol, nifursemizone, nifursol, nifurthiazole, nifurtimox, nifurtoinol, nifurvidine, nifurzide, nigludipine, nihydrazone, nikethamide, nileprost, nilprazole, niludipine, nilutamide, nilvadipine, nimazone, nimesulide, nimetazepam, nimidane, nimodipine, nimorazole, nimustane, neometacin, niperotidine, nipradilol, niprofazone, nitavoline, nirdazole, nisbuterol, nisobamate, nisoldipine, nisoxetine, nisterime, nitarsone, nitazoxanide, nitecapone, nithiamide, nitisinone, nitracrine, nitrafudan, nitralamine, nitramisole, nitraquazone, nitrazepam, nitrefazole, nitrendipine, nitrocefin, nitroclofene, nitrocycline, nitrodan, nitrofurantoin, nitrofurazone, nitromersol, nitromide, nitromifene, nitroscanate, nitrovin, nitroxinil, nitroxoline, nivazol, nivimedone, nizatidine, nizofenone, noberastine, nocloprost, nocodazole, nofecainide, nogalamycin, nolatrexed, nolinium, nolomirole, nolpitantium, nomegestrol, nomelidine, nomifensine, nonabine, nonaperone, nonapyrimine, nonathymulin, nonivamide, noracymethadol, norbolethone, norbudroine, norcholestenol, norclostebol, norcodeine, nordazepam, nordefrin, nordinone, norelgestromin, norepinepherine, norethandrolone, noethindrone, norethynodrel, noreximide, norfenefrine, norfloxacin, norgesterone, norgestimate, norgestomet, norgestrel, norgestrieneone, norletimol, norlevorphenol, normethadone, normorphine, norpipanone, nortetrazepam, nortopixantrone, nortriptyline, norvinisterone, nosantine, noscapine, nosiheptide, novobiocin, noxiptiline, noxytiolin, nuclomedone, nuclotixene, nufenoxole, nupafant, nuvenzepine, nylestriol, nylidrin, nystatin, obidoxime, ocaperidone, ocfentanil, ociltide, ocinaplon, octacaine, octafonium, octamoxin, octapinol, octatine, octaverine, octazamide, octenidine, octicizer, octimibate, octinoxate, octisalate, octocrylene, octodrine, octopamine, octotiamine, octreotide, octriptyline, octriazole, odalprofen, odapipam, odiparcil, ofloxacin, oformine, oftasceine, oglufanide, olaflur, olamufloxacin, olanexidine, olanzapine, olaquindox, olcegepant, oleandomycin, oletimol, olmesartan, olopatadine, olpadronic acid, olpimedone, olprinone, olradipine, olsalazine, oltipraz, olvanil, omaciclovir, omalizumab, omapartrilat, omeprazole, omidoline, omigapil, omiloxetine, omoconazole, omonasteine, onapristone, ondansetron, ontazolast, ontianil, opanixil, opaviraline, opiniazide, opipramol, opratonium, orazamide, orazipone, orbofiban, orbutopril, orconazole, orientiparcin, oritavancin, ormaplatin, ormeloxifene, ormetoprin, ornidazole, ornipreessin, ornithine, ornoprostil, orotic acid, orotirelin, orpanoxin, orphenadrine, ortataxel, orteteamine, osanetant, osaterone, oseltamivir, osemozotan, osmadizone, ospemifene, ostreogrycin, osutidine, otamixaban, otenzepad, oteracil, otilonium, otimerate, ouabain, oxabolon, oxabrexine, oxaceprol, oxacillin, oxadimedine, oxaflozane, oxaflumazine, oxagrelate, oxalinast, oxaliplatin, oxamarin, oxametacin, oxamisole, oxaminiquinem oxanamide, oxandrolone, oxantel, oxapadol, oxapium, oxaprazine, oxaprotiline, oxaprozin, oxcarbazole, oxatomide, oxazafone, oxazepam, oxazidone, oxazolam, oxazorone, oxcarbazepine, oxdralazine, oxeclosporin, oxedrine, oxeglitazar, oxeladin, oxendolone, oxepinac, oxetacillin, oxethazine, oxetorone, oxfendazole, oxfenicine, oxibendazole, oxibetaine, ociconizole, oxidapamine, oxidronic acid, oxfentorex, oxifungin, oxigluttione, oxilofrine, oxilorphan, oximonam, oxindanac, oxiniacic acid, operomide, oxiracetam, oxiramide, oxisopred, oxisuran, oxitefonium, oxitriptan, oxitriptyline, oxtriponium, oxmetidine, oxodipine, oxogestone, oxolamine, oxolinic acid, oxomermazine, oxonazine, oxophenarsine, oxoprosto; 1, oxpheneridine, oxprenoate, oxprenolol, oxtriphylline, oxbenzone, oxybutynin, oxychlorosene, oxycinchophen, oxyclipine, oxyclozanide, oxycodone, oxydipentonium, oxyfedrine, oxymesterone, oxymetazoline, oxymethalone, oxymorphone, oxypendyl, oxypertine, oxyphenbutazone, oxyphencyclimine, oxyphenisatin, oxyphenonium, oxypurinol, oxypurronium, oxyquinoline, oxyridazine, oxysonium, oxytetracycline, oxytocin, ozagrel, ozagamicin, ozolindone, paclitaxel, pacrindolol, pactimibe, padimate A, padimate Q, pafenolol, pagoclone, paldimycin, palinavir, paliperidone, palivizumab. palmidrol, palmoxirate, palonidipine, palonosertron, palosuran, parnabron, pamaqueside, pamaquin, pamicogrel, pamidronic acid, panadiplon, panamesine, pancopride, pancuronium, panipenem, panomifene, pantenicate, pantethine, panthenol, pantoprazole, panuramine, papverine, papveroline, parachlorphenol, paraflutizide, paramethadione, paramethasone acetate, paranitrosulfathiazole, paranyline, parapenzolate, parapropamol, pararosaniline, paraxazone, parbendazole, parcetasal, parconazole, parecoxib, pareptide, parethoxycaine, pargeverine, pargolol, pargyline, paricalcitol, paridocaine, parodilol, paromomycin, paroxetine, paroxypropione, parsalmide, particin, parvaquone, pasiniazid, pasireotide, patamostat, patupilone, paulomycin, paxamate, pazelliptine, pazinaclone, pazoxide, pazufloxacin, pecilocin, pecocycline, Pediarix®, pefloxocin, pegylated interferon alfa-2a, pegylated interferon alfa-2b, pelanserin, peldesine, peliomycin, pelitinib, pelitrexol, pelretin, pelrinone, pelubiprofen, pemedolac, pemerid, pemetrexed, pemirolast, pemoline, penamecillin, penbutolol, penciclovir, pendecamine, pendetide, penfluridol, penflutizide, pengitoxin, penicillamine, penicillin G, penicillin V, penimepicycline, penimocycline, penirolol, penmesterol, penoctonium, penprostene, pentabamate, pentacynium, pentfluranol, pentagastrin, pentagestrone, pentalamide, pentamethonium, pentamidine, pentamorphone, pentamoxane, pentamustine, pentapiperide, pentapiperium, pentaquine, pentazocine, pentetic acid, pentreotide, penthienate, penthrichloral, pentiapine, pentifylline, pentigetide, pentisomicin, pentisomeide, pentizidone, pentobarbital, pentolinium, pentolonium, pentomone, pentopril, pentorex, pentosalen, pentostatin, pentoxifylline, pentoxyverine, pentrinitrol, pentylenetetrazol, peplomycin, pepstatin, peraclopone, peradoxime, perafensine, peralopride, peramivir, peraquisin, perastine, peratizole, perazine, perbufylline, perfomedil, perfosfamide, pegolide, perhexiline, periciazine, perifosine, perimetazine, perindopril, perindoprilat, perisoxal, perlapine, permethrin, perospirone, perphenazine, persilic acid, perzinfotel, petrichloral, pexantel, phanquone, phenacaine, phenacemide, phenacetin, phenactropinium, phenadoxone, phenaglycodol, phenamazoline, phenampromide, phenaphthazine, phenarsone, phenazocine, phenazopyridine, phenbutazone, phencarbamide, phencyclidine, phendimetrazine, phenelzine, pheneridine, phenethicillin, pheneturide, phenylglutarimide, phenicarbazide, phenindamine, phenindione, pheniprazine, pheniramide, phenisonone, phenmetrazine, phenobarbital, phenobutiodil, phenomorphan, phenothiazine, phenothrin, phenoxybenzamine, phenoxypropazine, phenprobamate, phenprocoumon, phenpromethamine, phensuximide, phentermine, phentolamine, phenyl aminosalicylic acid, phenylalanine, phenylbutazone, phenylephrine, phenylpropanolamine, phenylthiolone, phenyltoloxamine, phenyracillin, phenyramidol, phenytoin, pnetharbital, pholcodine, pholedrine, phoxim, phthalofyne, phthylsulfacetamide, phthalylsulfamethiazole, phtha; lylsulfathiazole, physostigmine. Phytic acid, phytonadione, pibaxizine, pibecarb, piberaline, piboserod, pibrozelesin, pibutidien, picafibrate, picartamide, picenadol, picilorex, piclamilast, piclonidine, piclopastine, picloxydine, picobenzide, picodralazine, picolamine, piconol, picoperine, picoplatin, picoprazole, picotamide, picotrin, picumast, picumeterol, pidobenzone, pidolacetamol, pidolicaicd, pidotimod, pifarnine, pifinate, pifexole, piflutixol, piketoprofen, pildralazine, pilocarpine, pilsicainide, pimagedine, pimeclone, pimecrolimus, pimefylline, pimelautide, pimetacin, pimethixene, pimetine, imetremide, pimilprost, piminodine, pimobendan, pimonidazole, pimozide, pinacidil, pinadoline, pinafide, pinaverium, pinazepam, pincainide, pindolol, pinokalant, pinolcaine, pinoxepine, pioglitazone, pipacycline, pipamazine, pipamperone, pipazethate, pipebuzone, pipecuronium, pipemidicacid, pipendoxifene, pipenzolate, pipequaline, piperacetazine, piperacillin, piperamide, piperidolate, piperilate, piperocaine, piperonyl butoxide, piperoxan, piperphenidol, piperylone, pipobroman, pipoctanone, pipofezine, piposulfan, pipotiazine, pipoxizine, pipoxolan, pipradimadol, pipradrol, pipramadol, pipratecol, piprinhydrinate, pipocurarium, piprofurol, piprozolin, piquindone, piquizil, piracetam, pirandamine, pirarubicin, piraxelate, pirzmonam, pirazolac, pirbenicillin, pirbuterol, pirdonium, pirenoxine, pirenperone, pirezepine, pirepolol, piretanide, pirfenidone, pirbendil, piridicillin, piridocaine, piridoxilate, piridronic acid, pirifibrate, pirimiphos-ethyl, pirindazole, pirinixic acid, pirinixil, piriprost, piriqualone, pirisudanol, piritramide, piritrexin, pirlimycin, pirlindole, pirmagrel, pirmenol, pimabine, piroctone, pirodavir, priodomast, pirogliride, piroheptine, pirolate, pirolazamide, piromidic acid, piroxantrone, piroxicam, piroxicillin, piroximone, pirozadil, pirprofen, pirquinozol, pirralkonium, pirsidomine, pirtenidine, pitenodil, pitofenone, pituxate, pivagabine, pivampicillin, pivenfrine, pivopril, pivoxazepam, pixantrone, pizotyline, plafbride, plaunotol, plauracin, pleconaril, pleuromulin, plevitrexed, plicamuycin, plomestane, pobilukast, podilfen, podofilox, poldine, polymixin sulfate, polythiazide, pomisartan, ponalrestat, ponazuril, ponfibrate, porfiromycin, posaconazole, posatirelin, posizolid, poskine, practolol, pradolfoxacin, prajmalium, pralatrexate, pralidoxime, pralmorelin, pralnacasan, pramipexole, pramiracetam, pramoxine, prampine, pranazepide, pranidipine, prankulast, pranolium, pranoprofen, pranosal, prasterone, prasugrel, pratosartan, pravadoline, pravastatin, praxadine, prazarelix, prazepam, prazepine, praziquantel, prazitone, prazocillin, prazosin, preclamol, prednazate, prednazoline, prednicarbate, prednimustine, prednisolamate, prednisolone, prednisone, prednival, prednylidene, pregabalin, pregnadiol, pregnenolone, premafloxacin, premazepam, prenalterol, prenisteine, prenoverine, prenoxdiazine, prenylamine, pretamazium, pretiadoil, prevnarg, prezatide, pribecaine, pridefine, prideperone, pridinol, prifelone, prifinium, prifuroline, pilocalne, primaperone, primaquine, primidolol, primidone, primycin, prinomastat, prinomide, prinoxodan, pristinol, pristinamycin, prizidilol, proadifen, probarbital, probenecid, probicromil, probucol, procainamide, procaine, procarbazine, procaterol, prochlorperazine, procinolol, procinonide, proclonol, procromil, procyclidine, procymate, prodeconium, prodilidine, prodipine, prodolic acid, profadol, profexalone, proflavine, proflazepam, progabide, progesterones, proglumetacin, proglumide, proheptazine, proligestone, praline, prolintane, prolonium, promazine, promegestone, promestriene, promethazine, promolate, promoxolane, prontalol, propacetamol, propafenone, propagermanium, propamidine, propanidid, propanocaine, propantheline, proparacaine, propatyl nitrate, propazolamide, propenidazole, proprntofylline, propenzolate, properidine, propetamide, propetamfos, propetandrol, propicillin, propikacin, propinetidine, propiomazine, propiocaine, propiram, propisergide, propiverine, propizepine, propofol, propoxate, propoxur, propoxycaine, propoxyphene, propranolol, propyl docetrizoate, propyl gallate, propylhexedrine, propyliodone, propylthiouracil, propyperone, propyphenazone, propyromazine, proquazone, proquinolate, prorenoate, proroxan, prscillardin, prospidium, prostalene, prosulpride, prosultiamine, proterguride, protheobromine, prothipendyl, prothixene, protiofate, protionamide, protirelin, protizinic acid, protokylol, protoporphyrin, protriptyline, proxzole, proxibarbal, proxibutene, proxicromil, proxifezone, proxorphan, proxymetacaine, proxyphylline, prozapine, prucalopride, prulifloxacin, pruvanserin, pseudoephedrine, pumafentrine, pumaprazole, pumitepa, pumosetrag, puromycin, pyrabrom, pyrantel, pyrathiazine, pyrazinamide, pyrazofurin, pyricarbate, pyridarone, pyridinol, pyridofylline, pyridostigmine, pyridoxal, pyridoxamine, pyridoxine, pyrilamine, pyrimethamine, pyrimate, pyrinoline, pyrithione, pyrithyldione, pyritidium, pyritinol, pyrophenindane, pyrovalerone, pyroxamine, pyrrobutamine, pyrrocaine, pyrrolifene, pyrroliphene, pyrroInitrin, pyrroxane, pyrvinium, pytamine, quadazocine, quadrosilan, quatacaine, quazepam, quazinone, quazodine, quazolast, quetiapine, quifenadine, quiflapon, quillifoline, quilostigmine, quinacainol, quinacillin, quinacrine, quinagolide, quinaldine blue, quinapril, quinaprilat, quinazosin, quibolone, quincarbate, quindecamine, quindonium, quindoxin, quinelorane, quinestradol, quinestrol, quinethazone, quinetolate, quinezamide, quinfamide, quingestanol acetate, quingestrone, quinidine, quinine, quinotolast, quinpirole, quinterenol, quitiofos, quinuclium, quinupramine, quinupristin, quipazine, quisultazine, rabeprazole, raclopride, ractopamine, radafaxine, rafoxanide, ragaglitazar, ralitoline, raloxifene, raltitrexed, raluridine, ramatroban, ramciclane, ramelteon, ramifenazone, ramipril, ramiprilat, ramixotidine, ramnodigin, ramnoplanin, ramorelix, ramosetron, ranelic acid, ranimustine, ranimycin, ranirestat, ranitidine, ranolaine, rapacuronium, rasagiline, rasburicase, rathyronine, ravuconazole, razaxaban, razinodil, razobazam, razoxane, rebimastat, reboxetine, recainam, reclazepam, recombinant Factor VIII, recombinant human insulin, recothrome, regadenoson, reglitazar, relcovaptan, relomycin, remacemide, remifentanil, remikiren, remiprostol, remoxipride, renanolone, rentiapril, renzapride, repaglinide, reparixin, repinotan, repirinast, repromicin, reproterol, rescimetol, rescinnamine, resequinil, reserpine, resiquimod, resocortol butyrate, resorantel, resorcinol, retapamulin, retelliptine, retigabine, retinol, revaprazan, revatropate, revenast, reviparin, revizinone, revospirone, ribavirin, riboflavin, riboprine, ribostamuycin, ricasetron, ridazolol, ridogrel, rifabutin, rifalazil, rifametane, rifamexil, rifamide, rifampin, rifapentine, rifaximin, rilapine, rilmakalim, rilmazafone, rilmenidine, rilopirox, rilozarone, rilpovorine, riluzole, rimantadine, rimazolium, rimcazole, rimexolone, rimiterol, rimonabant, rimoprogin, riodipine, rioprostil, ripazepam, ripisartan, risarestat, risedronicacid, risedronate, risocaine, risotilide, rispenzepine, risperidone, ristianol, ristocetin, ritanserin, ritometan, ritipenem, ritobegron, ritodrine, ritolukast, ritonavir, ritropirronium, ritrosulfan, rituximab, rivaroxaban, rivastigmine, rivoglitazone, rizatriptan, robalzotan, robenidine, rocastine, rocepafant, rociclovir, rocuronium, rodocaine, rodorubicin, rofecoxib, rofelodine, rofleponide, roflumilast, rogletimide, rokitamycin, rolafagrel, roletamide, rolgamidine, rolicyclidine, rolicyprine, rolipram, rolitetracycline, rolodine, rolziracetam, romazarit, romergoline, romifenone, romifidine, romurtide, ronactolol, ronidazole, ronifibrate, fonipamil, runnel, ropinirole, ropitoin, ropivacaine, ropizine, roquinimex, rosaprostol, rosaramicin, rose bengal, rosiglitazone, rosoxacin, rostafuroxin, rostaporfin, rosterolone, rosuvastatin, rotamicillin, rotigotine, rotoxamine, rotaxate, roxadimate, roxarsone, roxatidine acetate, roxibolone, roxifiban, roxindole, roxithromycin, roxolonium, roxoperone, rubitecan, ruboxistaurin, rufinamide, rufloxacin, rupatadine, rupintrivir, rutamycin, ruvazone, ruzadolane, sabarubicin, sabcomeline, sabeluzole, sabiporide, saccharin, safingol, safirinol, sagandipine, salacetamide, salafibrate, salantel, salazodine, salazosulfadimidine, salazosulfamide, salazosulfathiazole, salbutamol, salcaprozoic acid, salcolex, salethamide, salflucerine, salicyl alcohol, salicylamide, salicylic acid, salinazid, salinomycin, salmefamol, salmeterol, salmisteine, salnacedin, salprotoside, salsalate, sameridine, samixogrel, sampatrilat, sampirtine, sancycline, sanfetrinem, sanguinarium, saperconazole, saprisartan, sapropterin, saquinavir, sarafloxacin, sarakalim, saralasin, sarcolysin, sardomozide, saredutant, saripedem, ssarizotan, sarmazenil, samoxicillin, sarpicillin, sarpogrelate, saterinone, satigrel, satranidazole, satraplatin, saviprazole, savoxepin, scopafungin, scopinast, scopolamine, secalciferol, seclazone, secnidazole, secobarbital, securinine, sedecamycin, sedoxantrone, seganserin, segesterone, seglitide, selamectin, selgiline, selfotel, soldenoson, selprazine, sampimod, sematilide, semaxanib, semduramicin, semorphone, semotiadil, semustine, senazodan, seocalcitol, sepazonium, seperidol, sepimostat, seprilose, seproxetine, sequifenadine, seratrodast, serazapine, serfibrate, sergolexole, sermetacin, sertindole, sertraline, setastine, setzindol, setipafant, setiptiline, setoperone, sevelamer, sevitropium, sevopramide, sezalamide, sagoside, sibenadet, sibopirdine, sibrafiban, sibutramine, siccanin, sifrprazine, siguazodan, silandrone, sildenafil, silibinin, silcristin, sildianin, silodosin, silodrate, silperisone, siltenzepine, simendan, simetride, simfibrate, simtrazene, simvastatin, sincalide, sinefungin, sinitrodil, sintropium, sipatrigine, siramesine, siratiazem, sirolimus, sisomicin, sitafloxacin, sitalidone, sitamaquine, sitaxentan, sitofibrate, sitoglusoide, sivelestat, soblidotin, sobuzoxane, solabegron, solifenasin, solimastat, solpecainol, solypertine, somatadine, somatostatin, somatropin, somatatropin, soneclosan, sonepiprazole, sopitazine, sopromidine, soquinolol, sorafenib, soraprazan, sorbinicate, sorbinil, sorivudine, sornidipine, sotalol, soterenol, spaglumic acid, sparfloxacin, sparfosate, sparsomycin, sparteine, spectinomycin, spiclamine, spiperone, spiradoline, spiramide, spiramycin, spirapril, spiraprilat, spirendolol, spirgetine, spirilene, spiriprostil, spirofylline, spirogermanium, spiroglumide, spiromustine, spironolactone, spiroplatin, spirorenone, spirotriazine, spiroxasone, spiroxatrine, spiroxepin, spizofurone, sprodiamine, squalamine, squalane, stacofylline, stllimycin, stannsoprfin, stanolone, stanoaolol, stavudine, stearylsufamide, steffimycin, stenbolone, strpronin, stercuronium, stevaladil, stibamine, stibophen, stilbamidine, stilbazium, stilonium, strimazole, stiripentol, stirocainide, stirofos, streptomycin, streptonicozid, streptonigrin, streptozocin, styramine, subathiazone, subendazole, succinylcholine, succinylsulfathiazole, succisulfone, suclofenide, sucralfate, sucralose, sucrose octaacetate, sucrosufate, sudexanox, sudoxicam, sufenatil, sufotidine, sufugolix, sugammadex, sulamserod, sulazepam, sulazuril, sulbactam, sulbenicillin, sulbenox, sulbentine, sulbutiamine, sulclamine, sulconazole, sulfabenz, sulfabenzamide, sulfacetamide, sulfachlorpyridazine, sulfachrysoidine, sulfaclomide, sulfaclorazole, sulfaclozine, sulfacytine, sulfadiazine, sulfadimethoxine, sulfadoxine, sulfaethidole, sulfaguanidine, sulfaguanole, sulfalene, sulfaloxic acid, sulfamazone, sulfamerazine, sulfameter, sulfamethaziine, sulfamethizole, sulfamethoxazole, sulfamethoxypyridazine, sulfametmidine, sulfametrole, sulfamonomethoxine, sulfamoxole, sulfanilamide, sulfanilate, sulfaanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinaolol, sulfinpyrazone, sulfiram, sulfisomidine, sulfisoxazole, sulfobromophthalein, sulfonterol, sulforidazine, sulfosalicylic aicd, sulfoxone, sulcrinat, sulindac, sulisatin, sulisobenzone, sulmarin, sulmazole, sulmepride, sulnidazole, sulocarbilate, suloctidil, sulodexide, sulofenur, sulopenem, sulosemide, sulotroban, suloxifen, sulpiride, sulprosal, suiprostone, sultamicillin, sultiame, sultopride, sultosilic acid, sultroponium, sulukast, sulverapride, sumacetamol, sumanirole, sumarotene, sumatriptan, sumetizide, sunagrel, suncillin, sunepitron, supidimide, supalast, suproclone, suprofen, suramin, suricainide, suriclone, suritozole, suronacrine, susalimod, suxemerid, suxethonium, suxibuzone, symclosene, synetine, tabilautide, tabimorelin, tacalcitol, tacapenem, tacedinaline, taclamine, tacrine, tacrolimus, tadalafil, tafluposide, taglutamine, tagorizine, talampanel, talampicillin, talaporfin, talastine, talbutal, tlaeranol, talibegron, talinolol, talipexole, talisomycin, tallimustine, talmetacin, talmetoprim, talnetant, talniflumate, talopram, talsalate, toloximine, talsaclidine, talsupram, taltirelin, taltobulin, taltrimide, taludipine, talviraline, tameridone, tameticillin, tametraline, tamibarotene, tamitinol, tanolarizine, tamoxifen, tampramine, tamsulosin, tanaproget, tandamine, tandospirone, tandutinib, taniplon, tanomastat, tapentadol, taprizosin, taprostene, tarazepide, tariquindar, tasosartan, tasuldine, taurolidine, tauromustine, tauroselcholic acid, taurosteine, tazadolene, tazanolast, tazarotene, tazasubrate, tazeprofen, tazifylline, taziprinone, tazobactam, tazofelone, tazolol, tazometine, tebanicline, tebatizole, tebipenem, tebufelone, tebuquine, tecadenoson, tecalcet, tecastemizole, teclthiazide, teclozan, tedisamil, tefazoline, tefenperate, teflufazine, teflutixol, tegafur, tegaserod, teglicar, teicopanin, telavancin, telbivudine, telenzepine, telinavir, telithromycin, telmesteine, telmisartan, teloxantrone, teludipine, temafloxacin, temarotene, tematropium, temazepam, temefos, temelastine, temiverine, temocapril, temocaprilat, temocillin, temodox, temoporfin, temozolomide, temisirolimus, temurtide, tenamfetamine, tenatoprazole, tendamistat, tenidap, tenilapine, teniloxazine, tenilsetam, teniposide, tenivastatin, tenocyclidine, tenofovir, tenofovir disoproxil, tenonitrozole, tenosal, tenosiprol, tenoxicam, tenylidone, teoprantil, teoprolol, tepirindole, tepoxalin, teprenone, teprotide, terazosin, terbequinil, terbinafine, terbogrel, terbucromil, terbufirol, terbuficin, terbuprol, terbutaline, terciprazine, terconazole, terdecamycin, terestigmine, terfeadine, terflavoxate, terfluranol, terguride, teriflunomide, terikalant, teriparatide, terizidone, terlakiren, terlipressin, temidazole, terodiline, terofenamate, teroxalene, teroxirone, tertatolol, tesaglitazar, tesicam, tesimide, tesimilifene, tesofensine, testolactone, testosterone, tetomilst, tetrabarbital, tetrabenazine, tetracaine, tetracycline, tetrahydrozoline, tetramethrin, tetramisole, tetraxetan, tetrazepam, tetrazolast, tetriprofen, tetrofosmin, tetronasin, tetroquinone, tetroxoprin, tetrydamine, teverelix, texacromil, tezacitabine, tezosentan, thalidomide, thebacon, thenalidine, thenium, thenyldiamine, theobromine, theodrenaline, theofibrate, theophylline, thiabendazole, thaicetarsamide, thialbarbital, thiamazole, thiamine, thiamiprine, thiamphenicol, thamylal, thiazesim, thiazinamium, thiazolsulfone, thiethyperazine, thihexinol ethylbromide, thimerfonate, thimerosal, thiocolchicoside, thioctic acid, thiofuradene, thioguanine, thiohexamide, thioinosine, thiopental, thiophanate, thiopropazate, thioproperazine, thioridazine, thiosalan, thiostrpton, thiotepa, thiotetrabarbital, thiothixene, thiphenamil, thiphencillin, thiram, thonzonium, thonzylamine, thozalinone, threonine, thymocartin, thymoctonan, thymol, thymopentin, thymotrinan, thyromedan, thyropropic acid, thyroxin, tiacrilast, tiadenol, tiafibrate, tiagabine, tiamenidine, tiametomnium, tiamulin, tianafac, tianeptine, tiapamil, tiapirinol, tiapride, tiaprofenic acid, tiaprost, tiaramide, tiazofurin, tiazuril, tiabalosin, tibeglisene, tibenelast, tibenzate, tibezonium, tibolone, tibric acid, tibrofan, ticabesine, ticalopride, ticarbodine, ticarcillin, ticlatone, ticlopidine, ticolubant, ticrynafen, tidembersat, tidiacic acid, tiemonium, tienocarbine, tienopramine, tienoxolol, tifemoxone, tifenazoxide, tiflamizole, tiflorex, tifluadom, tiflucarbine, tiformin, tifurac, tigecycline, tigemonam, tigestol, tigloidine, tilargenine, tiletamine, tilidine, tiliquinol, tilisolol, tilmacoxib, tilmicosin, tilnoprofen, tilomisole, tilorone, tilozepine, tilsuprost, tiludonic acid, timcodar, timefurone, timegadine, timelotem, timepidium, timiperone, timirdine, timobesone acetate, timofibrate, timolol, timonacic, timoprazole, tinabinol, tinazoline, tinidazole, tinisulpride, tinofedrine, tinoridine, tiocarlide, tioclomarol, tioconazole, tioctilate, tiodazosin, tiodonium, tiomergine, tiomesterone, tioperidone, tiopinate, tiopronin, tiopropamine, tiospirone, tiotidine, tiotropium, tioxacin, tioxamast, tioxaprofen, tioxidazole, tioxolone, tipentosin, tipepidine, tipetropium, tipifarnib, tipindole, tipranavir, tipredane, tiprenolol, tiprinast, tiprodil, tiprostanide, tiportimod, tiqueside, tiquinamide, tiquizium, tiracizine, tirapazamine, tiratricol, tirilazad, tirofiban, tiropramine, tisartan, tisocalcitate, tisocromide, tisopurine, tisoquone, tivanidazole, tiviciclovir, tivirapine, tixadil, tixanox, tixocortol, tizabrin, tizanidine, tizolemide, tizoprolic acid, tobicillin, toborinone, tobramycin, tocainide, tocamphyl, tocladesine, tocofenoxate, tocofibrate, tocophersolan, todralazine, tofenacin, tofetridine, tofimilast, tofisoline, tofisppam, tolafentrine, tolamolol, tolazamide, tolboxane, tolbutamide, tolvapone, tolciclate, toldimfos, tolfamide, tolfenamic acid, tolgabide, tolimidone, tolindate, toliodium, toliprolol, tolmesoxide, tometin, tolnaftate, tolnapersine, tolnidamine, toloconium, tolonidine, tolonium, toloxatone, toloxychlorinol, tolpadol, tolpentamide, tolperisone, tolpiprazole, tolpronine, tolpropamide, tolpyrramide, tolquinzole, tolrestat, tolterodine, toltrazuril, tolufazepam, tolvaptan, tolycaine, tomeglovir, tomelukast, tomoglumide, tomoxiprole, tonabersat, tonazocine, topilutamide, topiramate, topixantrone, topotecan, toprilidine, topterone, toquizine, torbafylline, torcetrapib, torcitabine, toremifene, toripristone, torsemide, tosagestin, tosifen, tosufloxacin, tosulur, trabectedin, traboxopine, tracazolate, tradecamide, tralonide, tramadol, tramazoline, trandolapril, trandolaprilat, tranexamic acid, tranilast, transcainide, trantelinium, tranycypromine, trapencaine, trapidil, trastuzumab, travoprost, traxanox, traxoprodil, trazitiline, trazium, trazodone, trazolopride, trebenzomine, trecadrine, trecetilide, trefentanil, trelnarizine, treloxinate, trenbolone, trengestone, trenizine, treosulfan, trepibutone, trepipam, trepirium, treprostinil, treptilamine, terquisin, tresperimus, trestolone, trethinium, trethocanoic acid, tretinoin, tretinoin tocoferil, tretoquinol, triacetin, triafungin, triamcinolone, triamcinolone acetonide, triamcinolone benetonide, triamcinolone furetonide, triampyzine, triamternem triaziquone, triazolam, tribendilol, tribenoside, tribromsalan, tribuzone, tricaprilin, tricetamide, trichlorfon, trichlormethiazide, trichlomethine, triciribine, triclabendazole, triclacetamol, triclazate, triclobisonium, triclocarban, triclodazol, triclofenol, triclofos, triclofyllin, triclonide, triclosan, tricyclamol, tridihexethyl, tridolgosir, trientine, triethylenemelamine, trifenagrel, trifezolac, triflocin, triflubazam, triflumidate, triflomeprazine, trifluperazine, trifluperidol, triflupromazine, trifluidine, triflusal, trifosmin, trigevolol, trihexylpheidyl, triletide, trilostane, trimazosin, trimebutine, trimecain, trimedoxime, trimegestone, trimeperidine, trimeprazine, trimetazidine, trimethadone, trimethamide, trimethaphan, trimethidinium, trimethobenzamide, trimethoprim, trimetozine, trimetrexate, trimexiline, trimipramine, trimoprostil, trimoxamine, trioxifene, trioxsalen, tripalmitin, tripamide, triparanol, tripelennamine, triplatin, triprolidine, triptorelin, tritoqualine, trixolane, trixoxime, trocimine, troclosene, trodusquemine, trofosfamide, troglitazone, troleandomycin, tromanttadine, tropabazate, tropanserin, tropapride, tropatepine, tropenziline, tropicamide, tropigline, tropirine, tropisetron, tropodifene, troquidazole, trospectomycin, trospium, trovafloxacin, trovirdine, troxacitabine, troxerutin, troxipide, troxolamide, troxonium, troxypyrrolium, truxicurium, truxipicurium, tryparsamide, tubocurarine, tubulozole, tucaresol, tuclazepam, tulathromycin, tulobuterol, tulopafant, turosteride, tuvatidine, tybamate, tykerb, tylosin, tymazolin, tyropanoate, tyrosine, tyrothricin, ubenimex, ubidecarenone, ubisindine, ufenamate, ufiprazole, uldazepam, ulifloxacin, uliprisnil, umespirone, undecylenic acid, unoprostone, upenazime, upidosin, uracil, uracil mustard, urapidil, uredepa, uredofos, urefibrate, ursodiol, urulcholic acid, utibapril, utibaprilat, vadocaine, valaciclovir, valconazole, valdecoxib, valdetamide, valdipromide, valethamate, valganiciclovir, valine, valnemulin, vlanoctamide, valofane, valomaciclovir, valperinol, valproate, valproate hemisodium (Depakote®) valproic acid, valpromide, valrocemide, valrubicin, valsartan, valorcitabine, valtrate, vamicamide, vancomycin, vandetanib, vaneprim, vanitiolide, vanoxerine, vanyldisulfamide, vapiprost, vapreotide, vardenafil, varenicline, varespladib, vatalanib, vatanidipine, vebufloxacin, vecuronium, vedaclidine, vedaprofen, velaresol, velnacrine, venlafaxine, venritidine, verodoline, veralipride, verapamil, verazide, verilopam, verlukast, verofylline, versetamide, verteporfin, vesnarinone, vestipitant, vetrabutine, vidarabine, vigabatrin, vilazodone, vildaglipin, viloxazine, vinbarbital, vinblastine, vinburnine, vincamine, vincanol, vincofos, vinconate, vincristine, vindeburnol, vindesine, vinpidine, vinflunine, vinformide, vinfosiltine, vinglycinate, vinleucinol, vinleurosine, vinmegallate, vinorelbine, vinpocetine, vinpoline, vinrosidine, vintiamol, vintoperol, vintriptol, vinylbital, vinzolidine, viomycin, viprostol, viqualine, viquidil, virginiamycin, viridofulvin, viroxime, visnadine, visnafylline, vofopitant, voglibose, volazocine, volpristin, voriconazole, vorozole, voxergolide, xaliproden, xamoterol, xanomeline, xanoxic acid, xanthinol, xantifibrate, xantocillin, xantofyl palmitate, xemilofiban, xenalipin, xenazoic acid, xenbucin, xenipentone, xenothiorate, xenygloxal, xenylhexenicacid, xenytropium, xibenolol, xibornol, xidecaflur, xilobam, ximelagatran, ximoprofen, xinidamine, xinomiline, sipamide, xipranolol, xorphanol, xylamidine, xylazine, xylocoumarol, xylometazoline, xyloxemine, yohimbic acid, zabicipril, zabiciprilat, zacopride, zafirlukast, zafuleptine, zalcitabine, zalderide, zaleplon, zalospirone, zalitidine, zaltoprofen, zamifenacin, zanamivir, zanapezil, zankiren, zanoterone, zapizolam, zaprinast, zardaverine, zatebradine, zatosetron, zelandopam, zenarestat, zenazocine, zeniplatin, zepastine, zeranol, zetidoline, zidapamide, zidometacin, zidovudine, zifrostilone, zilantel, zilascorb, zileuton, zilpaterol, zimeldine, zimiidoben, zindotrine, zindoxifene, zinconazole, zinostatin, zinterol, zinviroxime, zipeprol, ziprasidone, zocainone, zofenopril, zofenoprilat, zoficonazole, zolamine, zolasartan, zolazepam, zolendronic acid, (Zoledronate®), zolenzepine, zolertine, zolimidine, zoliprofen, zolmitriptan, zoloperone, zolpidem, zomebazam, zomepirac, zometapine, zonampanel, zoniclezole, zoniporide, zonisamide, zopiclone, zopolrestat, zorbamycin, zorubicin, zosuquidar, zotepine, zoticasone, zoxazolamine, zucapsaicin, zuclomiphene, zuclopenthixol, and zylofuramine, as well as pharmaceutically acceptable salts thereof, and mixtures thereof.

In contexts where open wounds are not at issue, but bandages are used for either topical or transdermal administration of compounds, the active agents that can be present can be virtually any active agent that is useful topically or transdermally. In addition, active agents which could not be previously administered transdermally because the drug transport was insufficiently high enough to deliver therapeutic levels can now frequently be used transdermally because larger areas of the body can be employed because the skin-contacting adhesive usually employed in transdermal products can be avoided. Thus, the type of active agent that can be employed in this context with the present invention is virtually unlimited (as the foregoing list suggests). In transdermal administration of active agents in this context, reservoir type transdermals, standard monolith type transdermals (where the monolith is an adhesive formulation) and monolithic transdermals where the monolith is non-skin-adhesive (adhesive, but not to skin) are all suitable. The present invention is particularly advantageous with non-skin-contacting-adhesive transdermals and reservoir type transdermals precisely because the skin contacting adhesive can be avoided. However, where a standard transdermal adhesive is desired, it can be used as long as the device is constructed so that there is a skin-non-adherent layer or material between the skin and the adhesive when the device is in use so that the skin is not in contact with a skin adherent adhesive.

In the particular embodiment used for circumcision wound healing in infants or pre-mature infants, clotting may not take place as efficiently as would in older children or adults. Thus, impregnating the central region 8 of device 1 with clotting Factors such as one or more of those set forth above, especially Factor VIII, Factor XII, and/or vitamin K or others known to be generally of use in promoting clotting helps to promote proper clotting and begin the healing process. Such bandages having clotting factors either impregnated therein or merely applied to the central portion skin contacting surfaces are also of use in treating wounds of known hemophiliacs. In such embodiments, the invention devices are significant improvements over the art in that while allowing for rapid local administration of various clotting factors, the bandages can be readily removed and changed without disturbing the clot so formed. Other patient populations for which such embodiments are particularly advantageous include diabetics, those with compromised immune systems (such as transplant patients, dialysis patients, those having radiation therapy or chemotherapy, radiation poisoning patients, and those presenting with HIV positive infection), and those with arthritis. The more rapid closing of the wound in these embodiments helps to protect against infection (extremely important for poor healers such as diabetics and immunocompromised patients and for use in settings where antibiotic resistant infectious organisms are likely present) and the design of the securement means as not being attached along the circumference, but rather protruding radially is of considerable benefit to those having arthritis in the hands or in the body part being bandaged. Similar application is suitable for other situations where clotting and homeostasis is being maintained. In situations where deep wounds are involved (such as, without limitation, battlefield injuries, emergency rooms, etc.), the devices of the present invention can be configured to deliver large quantities of homeostatic agents quickly and over a prolonged period by having such agents in multiple layers of biodegradable and/or hydrolyzable films such that the serum or other body fluid water contact acts to hydrolyze such films or to dissolve such materials so that they can reach further into the wound quickly.

The skin contacting surface of the central portion 8 can be replaced in whole or in part by a transdermal device which can be adhered to the innermost wall within central portion 8 by a suitable adhesive, or the transdermal formulation can be merely impregnated into the portions 20A, 20B, or linings 17 and 18. Since the devices of the present invention can cover significant areas of the body because they do not use skin-contacting adhesives (or if they do, such adhesive is prevented from contacting the skin), they can be used to administer active agents with lesser amounts of permeation enhancers than other transdermal devices known in the art, preferably substantially without penetration enhancers, most preferably without any. Furthermore, since the area of transdermal delivery can be large, the administration of drugs that are poorly administrable transdermally are possible to a greater degree, and the rate of permeation can be much lower so that prolonged transdermal administration of low flux is feasible. Unlike other transdermal devices known in the art, the present invention permits for lesser skin irritation due to less use of skin contacting adhesives and lesser use of skin permeation enhancers, yet the securement means maintains bandage/skin contact over large areas. Prior art "reservoir type" transdermal devices having adhesive only on the periphery of the device, did use lesser amounts of adhesive than monolithic type devices, but they suffered from the disadvantage that over large areas, the devices would not maintain optimal skin contact especially where body movement would create ripples in the skin. Even further, the larger areas that are now potentially able to be covered, would have been unacceptable with the skin-contact-adhesive devices of the art simply because removing such devices would be difficult and painful due to the presence of hairs. Even further, in situations where the transdermal permeability is adequate with a particular drug or formulation, occlusive dressings of most prior art transdermals becomes less of a concern and one can move to a breathable type of transdermal. The greater area for transdermal administration allows for a less efficient rate of permeation as when non-occlusive dressings are employed. Nonetheless, where desired, one will not depart from the present invention if one wishes to use the present invention in the context of a transdermal administration using permeation enhancers, skin-contacting adhesives (provided such adhesives are not in contact with skin surfaces), and/or occlusive materials.

In use, the bandages of the present invention are unfolded from one of the pre-use folded positions, and central portion 8 opened for receiving a body or plant part. If starting from the positions shown in FIGS. 6 and 7, pressure is placed on flaps 6 and 7 centrally. Depending upon the resiliency of the particular materials of which the device 1 is made, such central pressure may naturally open sleeve portion 11 or top portion 8 and bottom portion 9 may require some assistance to open into the correct orientation. The body part or plant part to which the bandage is to be applied is slipped into the sleeve portion and the flaps 6 and 7 are brought together while initially applying a slight amount of pressure on the top portion 9 of central portion 8 near the juncture of flaps 6 and 7 with central portion 8 allowing attachment means 12 and 13 to mate and secure the device in place. In a preferred embodiment, the body part to which the device is applied is an injured penis, more preferably a recently circumcised penis, most preferably a recently circumcised infant penis.

The preferred securement means is Velcro, but any securement means will be suitable. The fact that the securement means is not circumferentially attached about the body part means that in removing the bandage, the securement means can be undone without applying forces to the body or plant part being treated so as to reduce discomfort to the patient and have less of an undesired impact on the healing process while changing bandages than bandages which are secured circumferentially.

Figure 20:
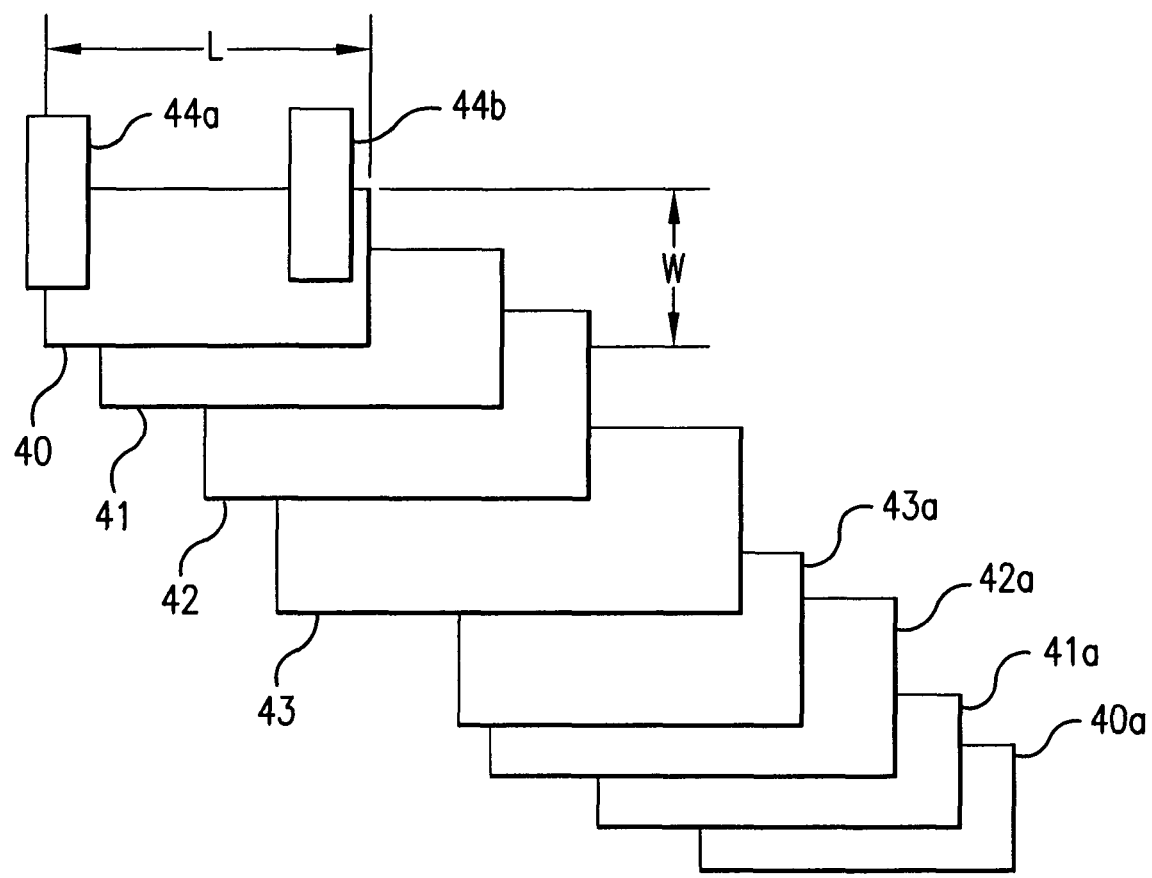
FIG. 20 shows an exploded view of another embodiment of the present invention.

In a further embodiment of the invention, one or more of the layers described above may actually be a multilaminate itself. A general exploded view of one embodiment of this type is shown in FIG. 20 where the device is laid out flat with layers 40-43 constituting a top portion (inclusive of securement means 44a and 44b) and layers 40a-43b constituting a bottom portion. Layers 43 and 43a are a skin-non-adherent layer and will be the skin contacting surface of the present invention. Layers 42 and 42a are an absorbent layer. Layers 41 and 41a are a waterproof material, and layers 40 and 40a are a decorative layer. Of these, the critical layer to have present is the non-adherent skin contacting layer or a coating of a skin non-adherent material that can be placed on the otherwise skin adherent material at any time prior to use so as to assure that the bandage is not skin-adherent. The only other important portion is the securement means and its placement outside of the central portion of the completed device so that the securement means from opposite portions of the device can be brought together in the manner described earlier. Securement means 44a and 44b may span across the entire width W or only a portion thereof, but preferably extends across the entire width W. In addition, one or both of securement means 44a and 44b need not be completely within the dimension L, but may optionally extend from within L to outside of L. Nonetheless, in preferred embodiments each of layers 41-43, 41a-43a and securement means 44a and 44b are all present. In a most preferred embodiment, layers 40 and 40a are also present.

Skin-non-adherent layers 43 and 43a (when no skin-non-adherent materials are added post manufacture) are typically comprised of non-adherent polyethylene or polypropylene apertured film, with the polyethylene film being preferred since the polypropylene material is more rigid. One such non-adherent polyethylene apertured film exemplary of the class is DelStar Delnet® polyethylene apertured film which is advantageously used in a thickness of about 1 to about 10 mils thick, preferably about 2 to about 8 mils thick, more preferably about 4 to about 6 mils thick. Other apertured films of other wound skin non-adherent materials are also possible and will be known to those of ordinary skill in the art. In addition, otherwise wound adherent materials may be utilized if they are suitable covered in the wound or skin contacting area with an ointment layer such as those made using a petrolatum base. Layers 43 and 43a may be coated with an ointment if desired (and is so if the fabric used is not a wound non-adherent material), and such ointment may contain active agents such as without limitation, antiseptics, anti-infectives, topical anesthetics, aids to clotting, and other wound healing materials. Alternatively, and especially when the layers 43 and 43a are inherently wound non-adherent, and therefore no ointment type covering in the skin contact layer is used, the layers 43 and 43a may be impregnated or have layered thereon one or more active agents such as without limitation, antiseptics, anti-infectives, topical anesthetics, aids to clotting, and other wound healing materials. In an alternative embodiment, layers 43 and 43a may be eliminated when the layers 42 and 42a are either themselves non-wound adherent or if layers 42 and 42a carry an ointment as described above to serve the wound non-adherent function.

Absorbent layers 42 and 42a are typically, but not required to be non-woven polyester pads and are present for the purpose of absorption of blood (in the case of human or animal wound dressings or of plant wound exudates in the case of plants wound dressings. One suitable alternative is polypropylene, but this is less advantageous because the polyester is the better absorber so that thinner layers could be used and it is economically more desirable as it is cheaper, has a nice bright white color for esthetic purposes, and it sterilizes well. One such polyester is DelStar non-woven polyester pad. The thickness of this layer will vary depending upon the absorption capacity of the exact material chosen and the absorption capacity thereof. Bandages for small wounds where less blood and exudates is anticipated will be able to be adequately addressed with relatively thinner layers, while those for larger wounds or for wounds where larger volumes of blood or exudates are anticipated will be better served with thicker layers and more absorbent layers 42 and 42a. Super absorbent materials that may also serve as alternatives for these layers include those absorbent materials utilized in disposable diapers, disposable undergarments, and sanitary napkins, which are well known in the art.

Waterproof layers 41 and 41a, while not absolutely required, are highly desirable. This is a thin flexible barrier layer to prevent leakage of blood or exudates out of the bandage, and when used in the context of an infant circumcision bandage aids in keeping urine from wetting the wound area. A typical exemplary waterproof material is a polyurethane film of about 0.5 to about 4 mils thick, preferably about 1 to about 2 mils thick. Other waterproof layer materials that can be suitably used include those used to line disposable diapers, disposable undergarments, and sanitary napkins. Occlusive barrier layers known in the transdermal drug delivery art are also suitable and may be used where desired for the waterproof layers 41 and 41a if so desired.

Decorative layers 40 and 40a are not required for the functioning of the device of the present invention but are generally present to provide both an overall aesthetic soft touch and to allow for printed matter such as an aesthetic design, instruction, or branding information. Spun laced fabric formed by hydroentanglement (used in a wide range of products such as hospital gowns, drapes, and bandages) is particularly suitable. Exemplary commercial materials include, without limitation, Dupont Sontara® or Dupont Softesse®. Again, outer layer printable soft materials utilized in commercially available disposable diapers, undergarments, and sanitary napkins are suitable alternatives if desired.

Securement means 44a and 44b are generally selected from hook and loop materials (usually known as Velcro), adhesives, snaps, and other generally known means of securing two materials together, hook and loop fasteners or adhesives being preferred, with loop and hook fasteners being most preferred. A highly preferred embodiment has Velcro as the securement means with one of 44a and 44b being the loop portion and the other being the hook portion.

In a most preferred embodiment, other than the securement means, the completed device is symmetric about the center line in terms of layers present, that is each of layers 40-43 that are present in the top portion has a corresponding layer 40a-43a representing the bottom portion and arranged in the same sequence as viewed from the center going toward the top and the center going toward the bottom. Nonetheless, there is no requirement that such symmetry be present for in all embodiments. In an exemplary manner of constructing the device of the invention, a symmetric embodiment will be employed, but the invention includes other manners of constructing the device whether or not such symmetry is present.

While the securement means 44a and 44b are shown in the figures at the left and right ends of flap portions 6 and 7 and cover the entire width of the flap (as viewed from front to back), the securement means is not required to traverse the full width of the flap portion, but preferably does. Thus, a securement means 44a or 44b may be for example only across a portion of the width of the flap and may be placed centrally (as viewed front to back) or off center either closer to the front or closer to the back (each as viewed from front to back) provided that the portions 44a and 44b are each placed in the same type of arrangement so that the portions 44a and 44b can mate when the bandage is in use. Additionally, flaps 6 and 7 are shown in the figures as being of the same length as viewed from central portion 8 towards the portion distal thereto either to the right or left. However, central portion 8 need not be at the center with two equal sized flaps extending therefrom. An arrangement where one of flaps 6 and 7 extends longer from central portion 8 than the other of flaps 6 and 7 is still within the scope of the present invention, as long as when flaps 6 and 7 are brought together, securement portions 44a and 44b can mate to effectively secure the bandage in place. Nonetheless, it is generally preferable to have flaps 6 and 7 extend for equal distances from central portion 8.

For an example of a manufacture of a bandage according to the invention; the following utilizes the embodiment having soft touch material layers 40 and 40a, waterproof layers 41 and 41a, absorbent layers 42 and 42a, wound non-adherent layers 41 and 41a, and Velcro securement means portions 44a and 44b. Individual rolls of the soft touch material, waterproof material, absorbent pad material, and wound non-adherent material are layered together in sequence and combined into a composite roll using heat seal, and/or pressure seal, and/or ultrasonic sealing techniques known in the art.

Adhesive sealing can also be used alone or in conjunction with any of the above but the use of adhesives between the absorbent layer and the wound non-adhesive layer would either require the adhesive being present only on the periphery or in some sort of pattern print to permit adequate permeation of fluids to the absorbent layer unless the adhesive is sufficiently permeable not to materially interfere with the function of the absorbent layer. Suitable adhesives and selective adhesive layer printing on a roll of material, as well as adhesives that are compatible with heat sealing, pressure sealing, and/or ultrasonic sealing techniques are well known in the transdermal art and one of ordinary skill can utilize any such materials and techniques in the manufacture of the present invention. Nonetheless, because of the selectivity of adhesives and the more expensive manufacturing techniques of selective printing of adhesives, it is preferable not to use adhesives between the absorbent layer and the wound non-adherent layer. The composites so formed may be (1) cut into appropriate width ribbons, the ribbons combined as below, and then cut into appropriate lengths or (2) the composites so formed may be combined as set forth below and then the combined intermediate cut into appropriate width ribbons, which are then cut into appropriate lengths. Either way, the composite (in this example having layers 40, 41, 42, and 43 along with any adhesive that may have been used, and having identical layer in reverse order, i.e., 43a, 42a, 41a, and 40a) are brought together with layer 43 facing layer 43a. Optional non-adherent ointment (with or without active agents) or an active agent solution may be applied to layers 43 and 43a either before they are brought together (and the operation may require a temporary release liner being utilized to roll the composite having such ointment or active solution applied thereto) or during the operation of combining the two composite rolls. The two rolls are adhered to each other via heat sealing and/or pressure sealing and/or ultrasonic sealing and/or adhesive sealing techniques known in the art such that central region 8 is not sealed, but the regions that will become flap portions 6 and 7 are sealed to each other. The result of this sealing operation then has the securement means 44a and 44b applied to one of layers 40 and 40a in the appropriate regions, which may be sealed thereto in any of the sealing manners mentioned above, namely, heat sealing and/or pressure sealing and/or ultrasonic sealing and/or adhesive sealing techniques. The end result is the cut in known manners (for example, without limitation as by die cutting or chopping) to the appropriately sized finished bandage.

Turning to the various auxiliary energy sources, as stated above, the dressing of the present invention can be coupled with or have incorporated therein iontophoretic, sonophoretic, photophoretic, and/or pulsed electronic systems. For both convenience and portability, where these systems are to be used, it is preferred to have them incorporated into the invention dressings, but where desired mere coupling the present invention with external devices to supply such driving forces is within the scope of the present invention.

A pulsed electronics system can be used for "electroporation" or opening up of the skin pores by the application of electronic pulses. An externally worn commercially available patch that accomplishes pulsed electronic application is available form BioElectronics Corporation under the name Acti-Patch, being commercialized as an aid for healing soft tissue (http://www.bioelectronicscorp.com). Such a device can be piggybacked on or incorporated directly into the present invention dressings with the pulsed electromagnetic delivery tuned to best open the pores for transdermal drug delivery. Alternatively, where iontophoretic delivery is desired, and the molecule being delivered is charged, a more or less constant electromagnetic delivery can be effected in the form of a magnetic or electric field that will force the drug through the skin. Other iontophoretic and electroporation systems for suitable coupling with or incorporation into the invention dressings include those disclosed by Swarbrick, et al Eds, *Encyclopedia of Pharmaceutical Technology* $2^{nd}$ ed., (Marcel Dekker, Inc. New York 2002), pp 1573-1587 and those disclosed by Sharma, et al; *Transdermal drug delivery using electroporation. I. Factors influencing in vitro delivery of terazosin hydrochloride in hairless rats*; Journal of Pharmaceutical Sciences 89:528-535 (2000). Ultrasonic delivery systems (sonophoretic) that can be coupled with or incorporated into the present invention dressings include those that are disclosed in Tang et al; *Effects of low-frequency ultrasound on the transdermal permeation of mannitol: Comparative studies with in vivo and in vitro skin*; Journal Pharmaceutical Sciences 91:1776-1794, 2002. Photophoretic systems for use in conjunction with or incorporated into the present invention dressings include those disclosed by Doukas, et al; *Transdermal drug delivery with photomechanical waves*; Lasers and Electro-Optics Society Vol. 1, No. 1, 1999; pp 360-361.

Liposomes are spherical vesicles having a hydrophobic membrane that encapsulates an aqueous or hydrophilic interior. Dissolved hydrophilic solutes cannot readily pass through the hydrophobic membrane. Hydrophobic solutes can be dissolved within the hydrophobic membrane. The liposome itself, as it has a hydrophobic exterior surface encounters much less resistance to transport across the skin than would the hydrophilic interior contents thereof. Delivery of the liposomes can take place by fusing with the hydrophobic portions of the skin lipid bilayer. Delivery of these formulations can be further enhanced by heating, such as by using concurrent energy sources such as are used in electroporation, iontophoresis, sonophoresis, and/or photophoresis.

Recently, nanoencapsulation has been found to allow for transdermal delivery of larger molecular weight molecules. Phosphagenics (an Australian company) was reported in June 2006 to have transdermally delivered insulin, PTH, and various proteins, as well as a number of smaller molecules by encapsulating them in a nanosphere of phosphorylated vitamin E. Use of this technology in the formulation of the particular drug formulation that is incorporated within the present invention dressings is contemplated, where desirable in order to further enhance the delivery of suitable materials. Although the US Food and Drug Administration has classified the technology as a "penetration enhancer" this technology is not within the "penetration enhancers" discussed above that preferred embodiments of the present invention avoid or minimize; rather, this delivery mechanism is specifically contemplated to be used with certain embodiments of the present invention dressings.

I claim:

1. A dressing comprising an upper and lower layer, defining therebetween, a central tubular portion and spaced apart flaps, said tubular portion having an inner surface which is designed to receive a body part or plant part therein; and said upper layer having a top surface distal from said inner surface and said lower layer having a bottom surface distal to said inner surface and distal to said top surface; and securement means on the top surface of said spaced apart flaps, such that when said top surfaces of said spaced apart flaps are brought together, face to face, said securement means on the respective top surfaces of said spaced apart flaps mate with each other and secure said dressing in place without either of said spaced apart flaps being circumferentially adhered to either said central portion or to said bottom surface whereby said dressing may be applied and removed without application of substantial torque to said body part or plant part.

2. The dressing of claim 1 further comprising one or more active agents.

3. The dressing of claim 2 wherein said active agent is selected from the group consisting of at least one (a) one or more anti-infective agents, (b) one or more local anesthetic agents, (c) one or more clotting agents, and mixtures thereof.

4. The dressing of claim 2 wherein said active agents are selected from the group consisting of blood clotting factors, local anesthetics, and antisepsis agents.

5. The dressing of claim 1 wherein said body part or plant part is a substantially cylindrical portion of the body.

6. The dressing of claim 5 wherein said body part is selected form the group consisting of a digit, a limb, the neck, the head, an ear, the body trunk, a breast, a penis, and the scrotal area.

7. The dressing of claim 1 wherein said dressing comprises from said inner surface outwards toward either said top surface or said bottom surface, a skin-non-adherent layer, an absorbent layer, and a waterproof layer.

8. The dressing of claim 7 wherein said wound dressing further comprises a decorative layer external to said waterproof layer.

9. The dressing of claim 1 wherein said securement means is selected from the group consisting of hook and loop fasteners, adhesives, snaps, self-adhesive material, and adhesive.

10. The dressing of claim 1 (a) having at least one human medicament incorporated therein or applied thereto prior to applying said dressing to a human body part; or (b) having at least one member selected from human and veterinary medicaments, and veterinary pesticidal agents incorporated therein or applied thereto prior to applying said dressing to an animal body part; or (c) having a at least one material selected from the group consisting of medications, herbicides, herbicide safeners, pesticides, pesticide safeners, plant growth factors, plant growth retardants, auxins, and mixtures thereof incorporated therin or applied thereto prior to applying said dressing to a plant part.

11. The dressing of claim 10 wherein at least one of said medicaments is a topical medicament.

12. The dressing of claim 10 wherein at least one of said medicaments is a systemically active medicament and said dressing is intended to delivery said systemically active medicament to the blood stream.

13. The dressing of claim 12, wherein said dressing delivers said systemically active medicament across intact skin.

14. The dressing of claim 12, wherein said systemically active medicament is administered transdermally, with or without auxiliary driving energy.

15. The dressing of claim 14 further comprising a transdermally driving energy generation device, incorporated therein or attached thereto.

16. The dressing of claim 15 wherein said transdermally driving energy source generation device is an iontophoretic device, a sonophoretic device, a photophoretic device, or a pulsed electronic device.

17. The dressing of claim 1 wherein said dressing has a transdermally administrable drug incorporated therein in a liposomal or nanoencapsulation format.

18. A method of administering a medicament to an open wound on a body part in the absence of an adhesive contacting the skin comprising incorporating said medicament in a dressing of claim 1 and applying said dressing to said wound and securing said dressing to said body part without the use of an adhesive in contact with the skin.

19. A method of transdermally administering a medication to a body part without the use of an adhesive in contact with the skin comprising incorporating said medication in the dressing of claim 1 and applying said dressing to said body part.

20. A method of avoiding or reducing skin irritation in a transdermal product having a transdermally administrable drug therein and a skin-adhering adhesive in contact with skin in the normal use of said transdermal product comprising incorporating said transdermal product into a dressing of claim 1 such that a skin-non-adherent layer that permits migration of said drug therethough is between said skin-adherent adhesive and said skin when said dressing is in use on said body part.

21. A method for reducing or eliminating skin irritation in a transdermal product having a transdermally administrable drug therein and a skin-adhering adhesive in contact with skin in the normal use of said transdermal product comprising omitting the use of said skin-adherent adhesive from said transdermal device to result in a modified transdermal device and incorporating said modified transdermal device into the dressing of claim 1 or utilizing the dressing of claim 1 to maintain the modified transdermal device in place on said body part.

22. A method of reducing or eliminating flux enhancer induced skin irritation in a transdermal device while maintaining the enhanced flux of a drug contained in said transdermal device, said transdermal device having at least one flux enhancer therein, comprising reducing, or eliminating said flux enhancers from said transdermal device and expanding the size of the transdermal device to cover a larger surface area to result in a modified transdermal device and incorporating said modified transdermal device into the dressing of claim 1 or utilizing the dressing of claim 1 to maintain the modified transdermal device in place on said body part.

* * * * *